(12) United States Patent
Cardosa et al.

(10) Patent No.: US 7,994,288 B2
(45) Date of Patent: Aug. 9, 2011

(54) ALLERGENIC PROTEINS OF NATURAL RUBBER LATEX, THEIR PRODUCTION AND USE IN ASSAYS

(75) Inventors: Mary Jane Cardosa, Penang (MY); Hamid Sharifah, Penang (MY); Shirley Samuel-Verghese, Kuala Lumpur (MY); Elumalai Sunderasan, Kuala Lumpur (MY); Hoong Yeet Yeang, Kuala Lumpur (MY); Hamzah Samsidar, Kuala Lumpur (MY)

(73) Assignees: The Board of the Rubber Research Institute of Malaysia, Kuata Lumpur (ML); Universiti Sains Malaysia, Kuala Lumpur (MY)

( * ) Notice: Subject to any disclaimer, the term of this patent is extended or adjusted under 35 U.S.C. 154(b) by 0 days.

(21) Appl. No.: 12/458,538

(22) Filed: Jul. 15, 2009

(65) Prior Publication Data
US 2009/0285859 A1   Nov. 19, 2009

Related U.S. Application Data

(62) Division of application No. 10/819,920, filed on Apr. 8, 2004, now Pat. No. 7,576,184, which is a division of application No. 08/529,152, filed on Sep. 15, 1995, now Pat. No. 6,759,517.

(30) Foreign Application Priority Data

Sep. 16, 1994   (MY) ................................. PI 9402468
May 4, 1995     (MY) ................................. PI 9501205

(51) Int. Cl.
*C12P 21/06*    (2006.01)
(52) U.S. Cl. ................................. 530/387.1; 530/388.1
(58) Field of Classification Search ........................ None
See application file for complete search history.

(56) References Cited

FOREIGN PATENT DOCUMENTS

WO          95/07298       3/1995

OTHER PUBLICATIONS

Campbell et al. 'Monoclonal antibody technology.' Elsevier Science Publishers. New York: 1984. Chapter 1, p. 29.*
C. Morales et al., *Clinical and Experimental Allergy*, 19, pp. 425-430 (1989).
Beezhold et al., *Clin. Exp. Immunol.* 98: pp. 408-413 (1994).
Todt et al., *J. Allergy Clin. Immunol.*, 93:1(2), 288, Abstract 721 (1994).
Akarawa et al., *J. Allergy Clin. Immunol.*, 93, 288, Abstract 723 (1994).
Czuppon et al., *J. Allergy Clin. Immunol.* 92:5, pp. 690-697 (1993).
Slater et al., *J. Allergy Clin. Immunol.*, 93:5, 825-830 (1994).
Sunderson et al., *J. Nat. Rubb. Res.* 10(2),p p. 82-99 (1995).
Hasma et al., *J. Nat. Rubb. Res.*, 7(2), pp. 102-112 (1992).
Alenius et al., *J. Allergy Clin. Immunol.* 93(5), pp. 859-863 (1994).
Alenius et al., *Int. Arch. Allergy Appl. Immunol.*, 96(4), pp. 376-380 (1991).
Kurup et al., *J. Allergy Clin. Immunol.*, 92(5), pp. 638-643 (1993).
Tata et al., *J. Nat. Rubb. Res.*, 28(2), pp. 67-76 (1980).
Campbell et al., *Monoclonal Antibody Technology*, Elsevier Science Publishers: New York, NY (1984), Chapter 1, p. 29.

* cited by examiner

*Primary Examiner* — Nora Rooney
(74) *Attorney, Agent, or Firm* — Wenderoth, Lind & Ponack, L.L.P.

(57) ABSTRACT

This invention relates to allergenic proteins of natural rubber latex in substantially purified form, their production and their use, together with monoclonal antibodies developed against those allergenic proteins, in assays for the qualitative and quantitative determination of the levels of the allergenic proteins in natural rubber latex or in products made from latex. Assays for identifying and/or quantitating antibodies in blood or blood products that mediate the occurrence of an allergic reaction induced by natural rubber latex are also provided, together with in vivo and in vitro diagnostic tests for detecting hypersensitivity to natural rubber latex and which involve use of the aforesaid allergenic proteins. The invention also provides for the use of the aforesaid allergens as de-sensitising agents in the treatment of latex protein allergy. There is still further provided a method for removing allergenic proteins from latex products.

1 Claim, 18 Drawing Sheets

Figure 1:
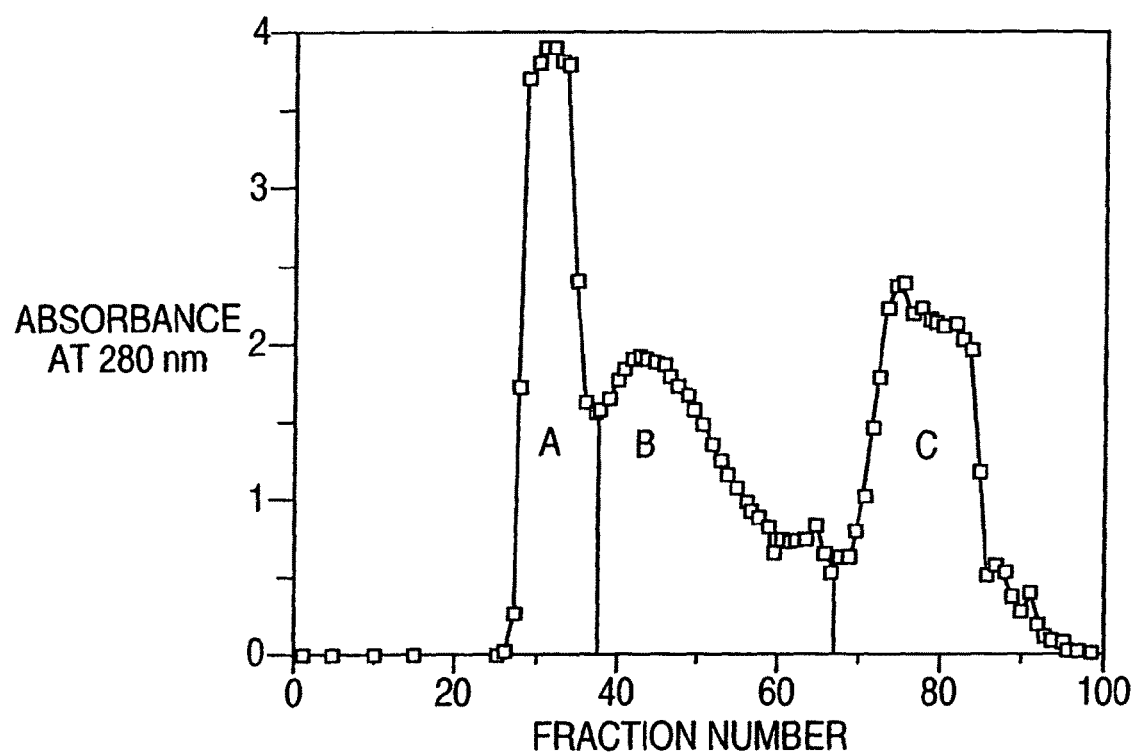

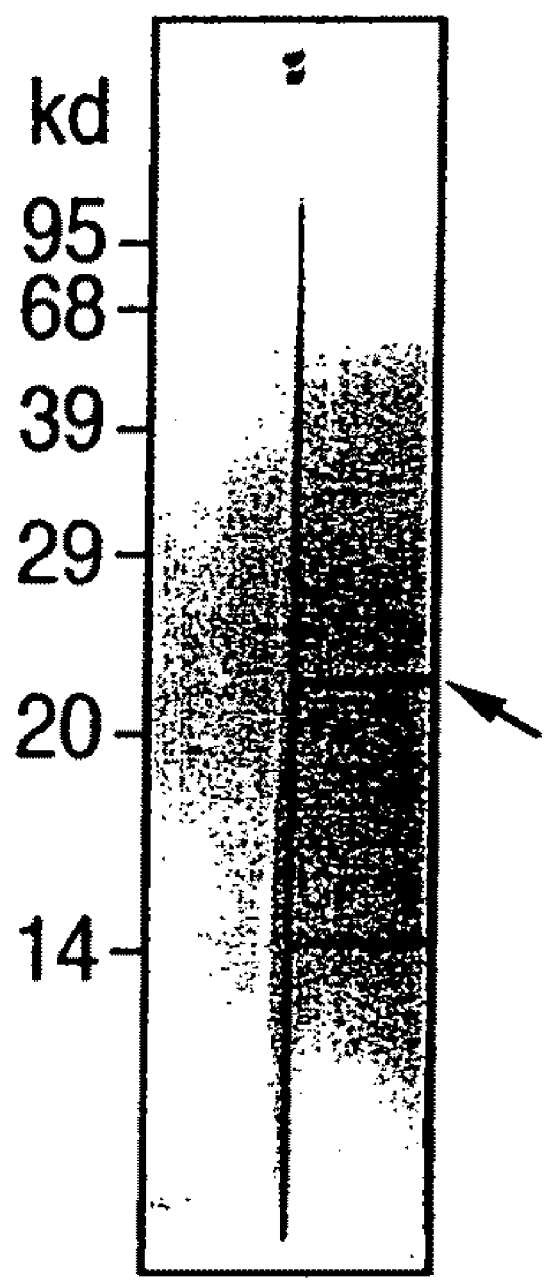
FIG. 3.1

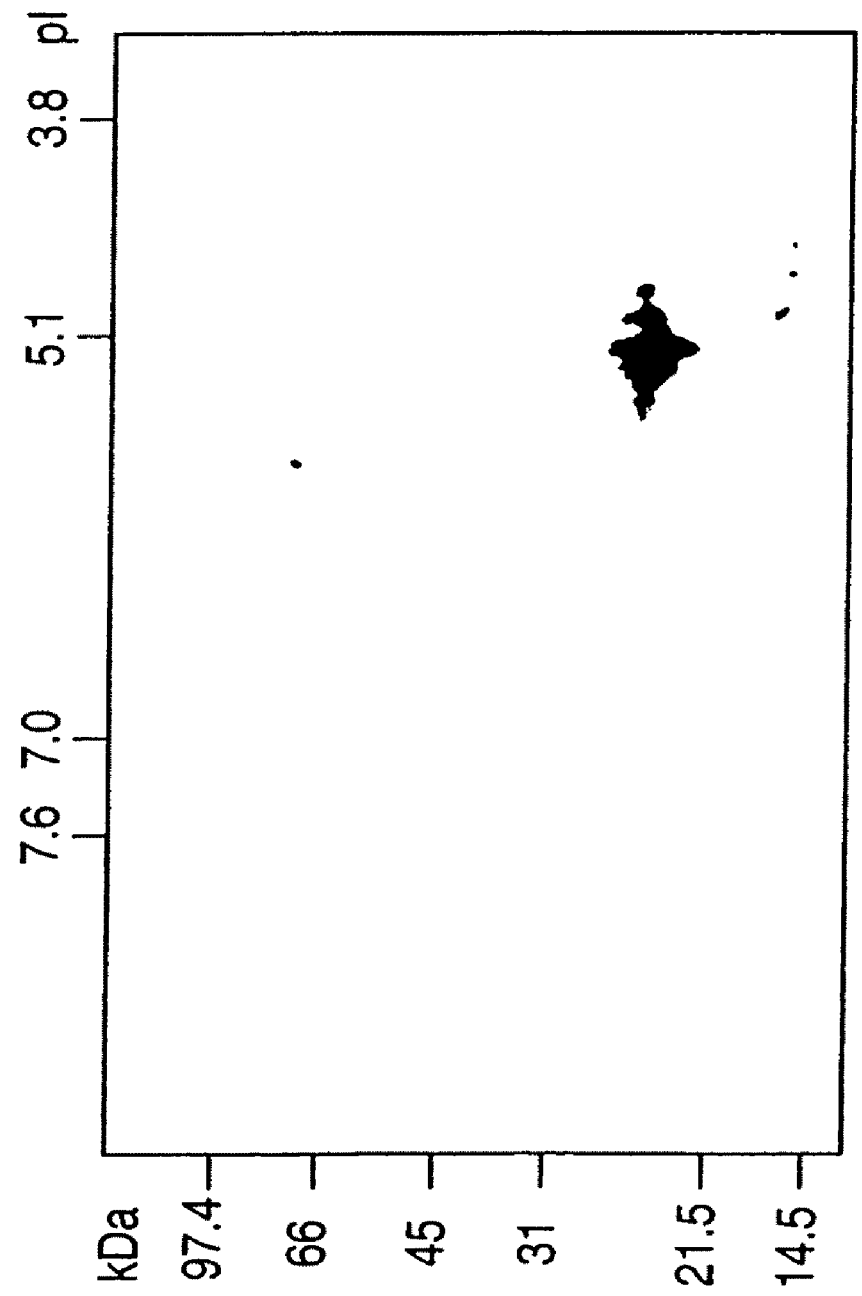

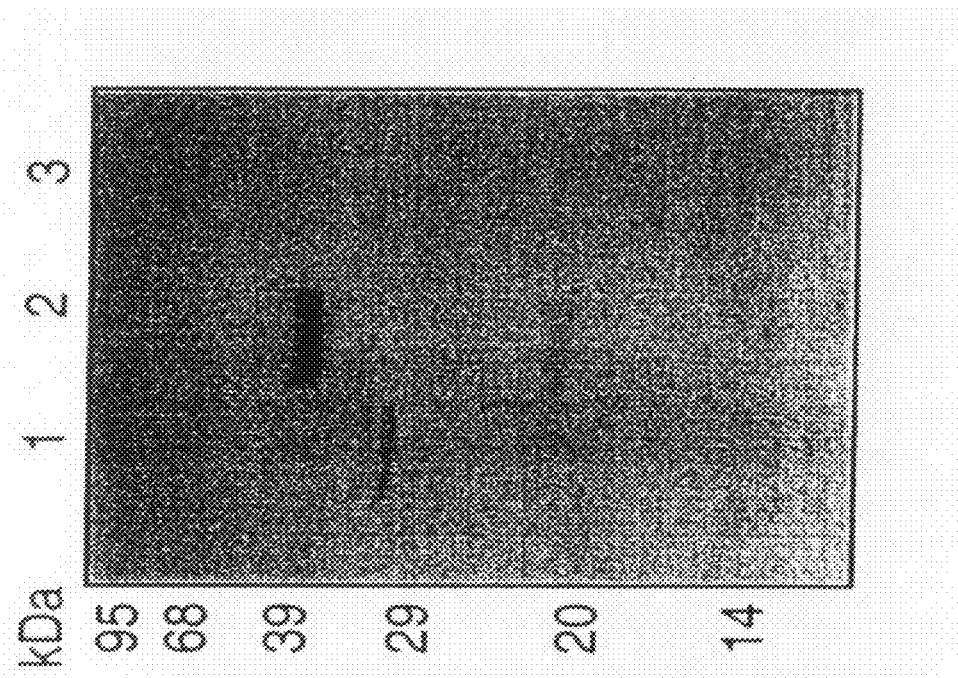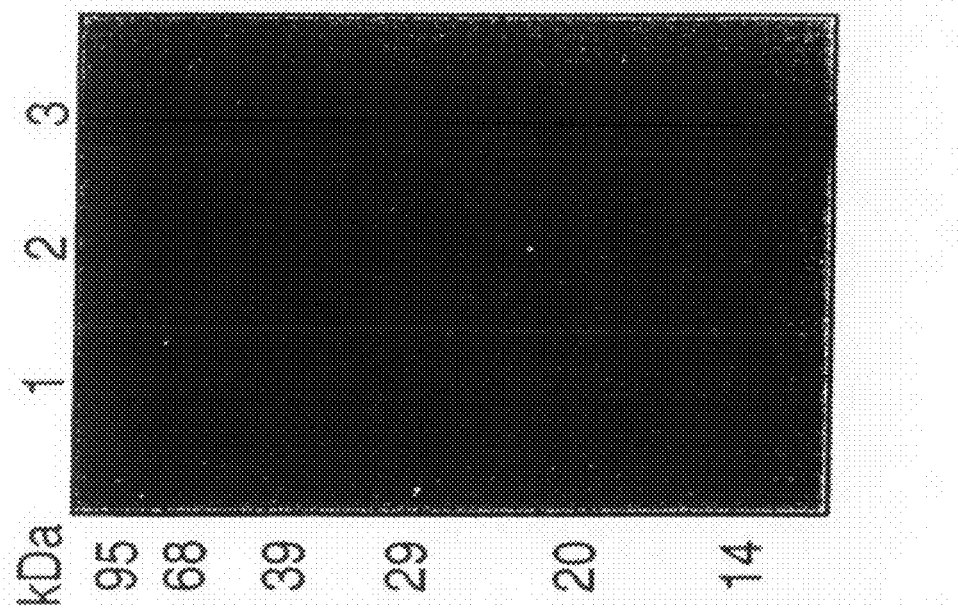

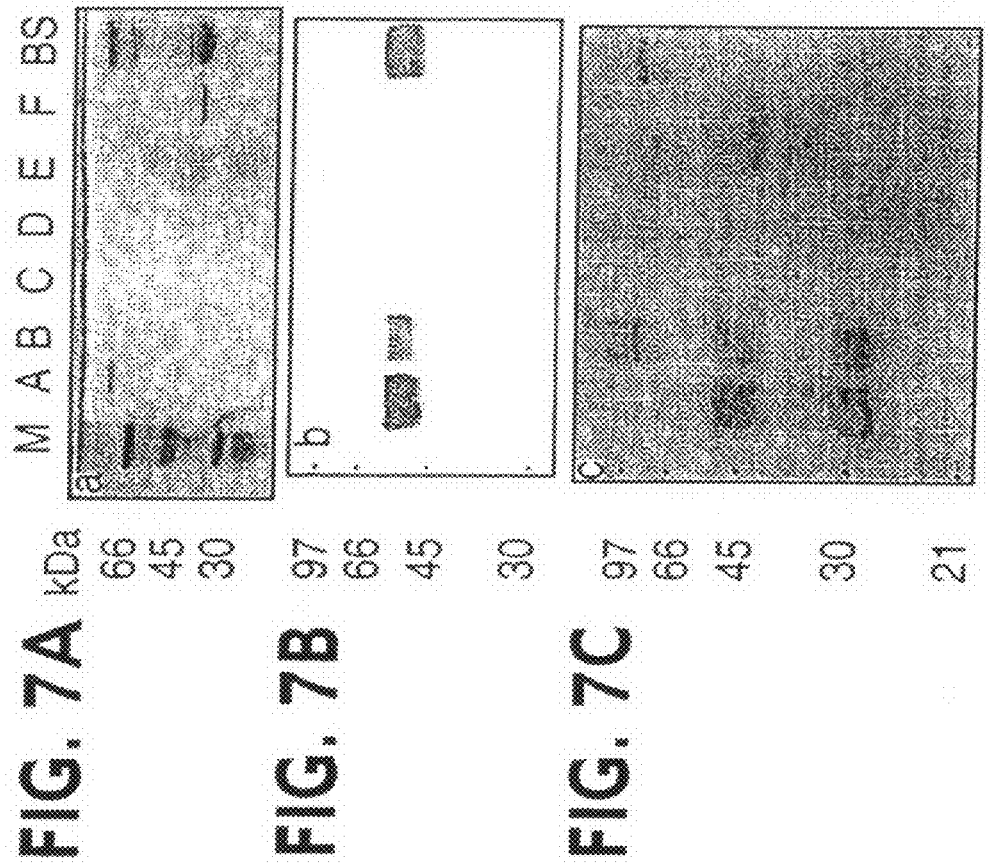

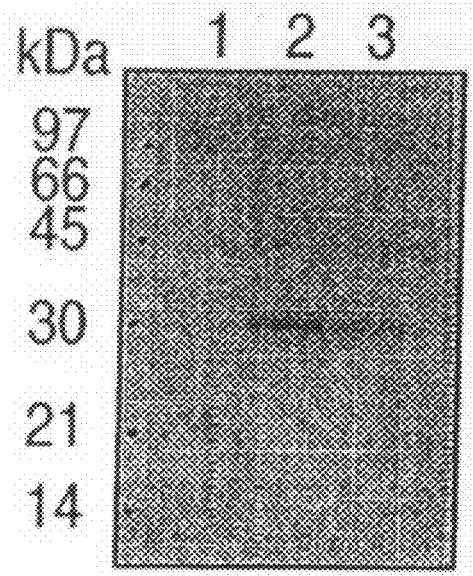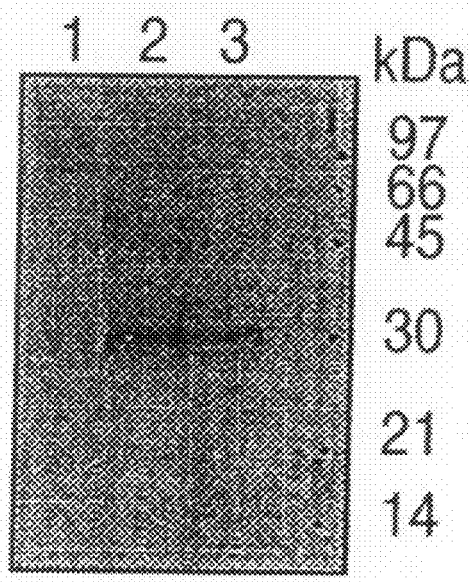

ALLERGENIC PROTEINS OF NATURAL RUBBER LATEX, THEIR PRODUCTION AND USE IN ASSAYS

This application is a divisional of Ser. No. 10/819,920, filed Apr. 8, 2004 now U.S. Pat. No. 7,576,184, which is a division of Ser. No. 08/529,152 filed Sep. 15, 1995, now U.S. Pat. No. 6,759,517, herein incorporated by reference in their entirety.

This invention relates to allergenic proteins of natural rubber latex in substantially purified form, their production and their use, together with monoclonal antibodies developed against those allergenic proteins, in assays for the qualitative and quantitative determination of the levels of the allergenic proteins in natural rubber latex or in products made from latex. Assays for identifying and/or quantitating antibodies in blood or blood products that mediate the occurrence of an allergic reaction induced by natural rubber latex are also provided, together with in vivo and in vitro diagnostic tests for detecting hypersensitivity to natural rubber latex and which involve use of the aforesaid allergenic proteins. The invention also provides for the use of the aforesaid allergens as de-sensitising agents in the treatment of latex protein allergy. There is still further provided a method for removing allergenic proteins from latex products.

There now follows a glossary defining certain of the terms used hereinafter:—

Total protein: All protein and fragments thereof present in a sample.
Antigenic proteins: A group within total proteins. These proteins elicit antibody production in the animal and human body. The antibodies elicited might include those of the IgE class which are able to induce an allergic reaction and also those that do not induce allergy. "Antigenic proteins" can also refer to proteins that are recognised by (react with) antibodies.
Allergenic proteins: A group within antigenic proteins (and hence a sub-group within total proteins). These proteins elicit production of the IgE class of antibodies in the animal or human body. They can induce an allergic reaction where IgE specific to them are present. "Allergenic proteins" can also refer to proteins that are recognised by (react with) IgE.
Allergens: Substances (proteins or otherwise) that elicit production of the IgE class of antibodies in the animal or human body. They can induce an allergic reaction where IgE specific to them are present. "Allergens" can also refer to substances that are recognised by (react with) IgE.
With regard to latex protein allergy, the only known allergens are proteinaceous in nature. Hence, in this context, the terms latex allergens, allergens, allergenic proteins and protein allergens are synonymous.
Antibodies: Immunoglobulins present in the serum of an animal and synthesised by plasma cells in response to an antigen.
IgE: A group within antibodies. IgE specific for an allergen is elicited in the animal or human body by its exposure to the allergen. Subsequent exposure to the allergen may induce an allergic reaction.
Polyclonal antibodies: A collection of antibodies against a particular antigen. Since most antigens have a large number of epitopes, there can be many different antibodies against a given antigen.
Monoclonal antibody: An immunoglobulin (antibody) produced by a single clone of lymphocytes. A monoclonal antibody recognizes only a single epitope on an antigen.
Epitope: An antigenic determinant in a molecule which is specifically recognised by an antibody combining site or by the antigen receptor of a T-cell.
Hybridoma: A cell line obtained by the fusion of a myeloma cell line, which is able to grow indefinitely in culture, with a normal antibody secreting B-cell. The resulting cell line has the properties of both partners, and continues to secrete the antibody product of the normal B-cell. By selecting a myeloma that has ceased to make its own immunoglobulin product, but has retained the machinery for doing so, the hybridoma secretes only the normal B-cell antibody. Since the cell line is cloned, the antibody is monoclonal.

Allergenic proteins (allergens) can induce an allergic reaction in sensitised persons which, in severe cases, can lead to an anaphylactic shock that is potentially lethal. Proteins present in latex products, such as latex gloves, can induce a form of allergy known as "Type I hypersensitivity" in a small proportion of people who use such products. The use of, rubber products, especially dipped latex products, is therefore being viewed with some caution and concern from the healthcare viewpoint.

Natural rubber from the commercial rubber tree, *Hevea brasiliensis*, is an important commodity in the economies of many Asian and African countries. Natural rubber is marketed in the form of bales, sheets and as latex concentrate. A major demand for natural rubber latex concentrate is in the manufacture of "dipped-latex" products such as gloves for examination, surgical and domestic use. In 1993, Malaysia alone exported latex dipped goods valued at a total of US$880 million. The global demand for latex examination gloves in particular has increased significantly in recent years with the rise in the incidence of the Acquired Immuno-deficiency Syndrome (AIDS) due to HIV infection.

There have been recent reports that gloves and other surgical aids manufactured from natural rubber latex can cause contact urticaria which, in a few cases, has led to anaphylactic reactions in persons previously sensitised (Nutter, 1979; Turjanmaa et al., 1984; Axelsson et al., 1987; Leynadier et al., 1989). Anaphylaxis can be life-threatening and is therefore far more serious than the generally mild skin sensitivities caused by the various chemical compounds used in glove manufacture. While contact dermatitis arising from chemicals has been recognized for many years, the allergic response to proteins in latex products such as gloves and catheters poses a potentially serious threat to their users. Those most at risk are health care workers, who may wear latex gloves more or less continuously throughout their working day, and their patients. Ultimately, the product manufacturers and the latex industry as a whole will feel the repercussions from the perceived threat, even though the proportion of people that are actually at risk is very small. Regulatory agencies such as the US Food and Drug Administration (FDA) have already indicated that they will require all natural latex goods to be identified as such in the near future. The US FDA may also soon be setting standards for acceptable levels of total protein in latex products. If this problem is not addressed with the urgency it deserves and means established to distinguish between "safe" and "unsafe" products, it is even possible that future legislation could impose a blanket ban on the use of all latex products in medical care.

Latex protein allergy has therefore been regarded with increasing concern in recent years, especially by the manufacturers of latex products and by those involved in healthcare. Evidence has pointed to water-extractable proteins in latex as the cause of the latex-induced anaphylactic reaction which is mediated through an interaction between allergenic latex proteins and a class of antibodies (IgE), in the sensitised person. IgE specific immunoassays of protein fractions have suggested that more than one specific protein may be involved (Turjanmaa et al. 1988; Slater, 1991).

In view of the importance of the latex protein allergy problem, both from the healthcare perspective and from the viewpoint of latex product manufacturers, active research in this connection is being undertaken in various laboratories worldwide. The main objectives of the investigations are:

(a) To produce a latex concentrate containing lower levels of allergens. Latex concentrate suppliers are seeking to reduce allergens in the source material used for the manufacture of latex products.

(b) To manufacture a low allergen latex product. Latex product manufacturers are seeking to reduce allergens in their finished products.

(c) To develop an assay for the quantitation of allergens present in latex concentrate or in products. Both the latex suppliers as well as latex product manufacturers require an assay for the purpose of standardisation and quality control to complement (a) and (b).

In the conventional preparation of latex concentrate, field latex is stabilised with ammonia (to prevent flocculation or coagulation of the rubber) and then concentrated by centrifugation to increase the rubber content from about 33% to 60%. Currently, there are two main approaches to the production of a low protein latex concentrate (Subramaniam, 1992). Firstly, multiple centrifugations can be carried out with fresh ammoniated water added in each cycle to dilute out the soluble proteins in the aqueous phase of the latex. Secondly, the latex can be treated with a protein-degrading enzyme (proteinase).

To manufacture latex-dipped products with reduced soluble proteins, the simplest method is to wash in water. Proteins migrate to the surface of the latex film as it dries (Shamsul Bahri et al., 1993) and are hence most effectively removed when the film is washed after complete drying.

While the above-mentioned measures are aimed at reducing the amount of allergens in the latex concentrate or in the finished latex product, there is at present no reliable way to assess the level of such allergens. In the absence of a specific latex allergen assay, samples are currently tested for total protein on the assumption that low total protein levels would be an indication of low allergen levels. This is generally true when comparing extreme protein levels (i.e. very high protein levels are associated with high allergenicity and very low protein levels are associated with low allergenicity). However, total protein levels can sometimes give a misleading picture as to how potentially harmful a product can be because not all proteins are allergenic (i.e. able to induce an allergy); many are innocuous. A better assay would be one that estimates the level of the latex allergens specifically.

Assays for latex allergens are commercially available and come in a number of variations, but they are all based on one or more immunological reactions of an immunoassay. An immunoassay is based on the interaction between antibodies with the specific protein antigens to which the antibodies will bind. Hence, in the case of an immunoassay for latex allergens, the principal reaction is the binding of latex allergens with the antibodies that recognise such allergens.

Assays based on the immune reaction relating to the latex allergy problem fall into two categories. In the first category, the assays quantitate the antibodies (IgE) in a blood sample that mediate the occurrence of an allergic reaction. Essentially, such assays are for healthcare and medical use and they serve as diagnostic tests for latex allergy. The second category of immunoassays pertains to the quantitation of latex allergens extractable from latex products. Essentially, such assays are for use in the latex industry to monitor and regulate the levels of latex allergens in latex concentrate and in manufactured latex products. Presently, there are a small number of commercially available immunoassays for both categories of tests.

Commercial immunoassays in RAST (radioallergosorbent test) and ELISA (Enzyme-linked immunosorbent assay) formats are used to determine if specific IgE to the latex proteins is present and, hence, test for latex allergy in patients. Such tests can also be performed as competitive assays (RAST inhibition, competitive ELISA) to quantitate the amount of allergen in a latex sample or a latex product.

All these immunoassays require the use of specific latex allergens in the immunological reaction. Since no latex allergens have so far been isolated and conclusively identified, the presently available commercial assays use as their allergen source crude (unpurified) latex serum or proteins eluted from commercially manufactured latex gloves.

Crude latex serum is unreliable as a source of allergens, however, because it contains a lot of proteins (and other substances) other than the allergens themselves. These impurities might interfere with the precision of the assay. There is also no information as to the level or consistency of the allergens in latex obtained from different sources, from different times of the year or latex that has been preserved or stored under different conditions. While the variation in allergenic protein levels in different batches of latex has not been investigated, latex proteins in general, and latex enzymes (a class of proteins) in particular, are known to vary with clonal (cultivar) source, season, physiological state of the tree, the intensitiy of tapping (latex harvesting) and the use of chemical stimulants to promote latex yield. For example, differences in latex proteins sourced from different commercial clones were discerned after electrophoretic separation (Walujono and Suseno 1973, Yeang et al., 1977, Prematillake and Yapa, 1985), indicating that protein composition varied between clones. The fact that some of these differences could be traced to latex B-serum proteins (Yeang et al., 1977) is significant in view of the fact that, as has now been discovered by the inventors of the present invention, some of the major latex allergens originate from the B-serum. Latex protein composition could also be influenced by the physiological state of the tree. Prematillaka et al. (1985) reported the disappearance or reduction of a number of latex proteins collected To from trees afflicted with the physiological disorder known as brown bast.

Differences in the iso-forms of enzymes of latex obtained from various commercial, *Hevea* clones have also been demonstrated (Chevallier, 1988) The activities of certain latex enzymes vary significantly with season (Yeang and Paranjothy, 1982). Moreover, latex enzyme activities are known to change significantly in response to the intensity of latex harvest (Yeang and Paranjothy, 1982a) and to yield stimulation by the chemical ethephon (Tupy, 1969; Chrestin et al., 1985). The level of a latex protein complex known as a microhelix has been reported to increase in the B-serum as a result of ethephon stimulation (Gomez and Moir, 1979). The microhelix has also been shown to be very variable and sometimes undetected in B-serum. This variation occurs between clones and also between samples taken at different times from the same group of trees (Gomez and Moir, 1979; Gomez and Tata, 1977). The last mentioned point is significant in view of the finding described below that one of the identified latex allergens is a component of the microhelix complex.

As mentioned above, proteins eluted from commercial latex gloves are also used as the protein antigen component of immunoassays for the diagnosis of latex allergy or for the quantitation of latex allergens. A serious drawback of this approach is that different brands of gloves (or even different batches of the same brand) show qualitative and quantitative differences in their allergen composition. As such, test results from assays that utilise latex glove proteins as antigens can vary considerably depending on the choice of latex gloves from which the antigens were sourced.

Not surprisingly, the commercially available latex allergen assays lack sensitivity and specificity and are only partially successful in detecting allergenicity.

Working with a commercially available latex antigen preparation, (supplied by Stallergenes), Levy (1993) reported that it gave positive results in 100% of sensitive patients and negative results in non-sensitive control patients. In another study (Lagier et al., 1992), however, 80% of test patients (nurses) who were known to be allergic to latex gave negative results with the commercial Stallergenes kit. From a study of forty allergic patients (diagnosed by skin prick tests), Leynadier, Autegard and Levy (1993) reported 5-16% false negative results with Stallergenes latex allergen as well as two other commercial allergens, supplied by Allerbio and Bencard. Hence, false negative results occur with the commercial latex allergens currently available. The most widely used RAST kit is probably the latex RAST k82 produced by Pharmacia Diagnostics and its enzyme-linked immunosorbant assay (Pharmacia CAP system). Levy (1993) reported that these assays were capable of detecting IgE antibody in the serum of 40-90% of skin prick test-positive latex-allergic patients.

Another commercially available immunoassay for latex allergens is the "Latex ELISA for Antigenic Proteins" (LEAP) manufactured by the Guthrie Research Institute, U.S.A. (Beezehold, 1993). The assay is based on an indirect ELISA (enzyme-linked immunosorbent assay) in which polyclonal antibodies against latex proteins are used. Such an assay might not be sufficiently effective in discriminating latex protein antigens in general (i.e. proteins that bind both to the allergy-inducing antibodies (IgE) and the non allergy-inducing antibodies) from the latex allergens (i.e. proteins that bind to IgE specifically). The use of this assay also assumes that all antigens and allergens bind equally well to the ELISA plate under the same conditions since the test samples containing the antigens/allergens to be determined are required to be bound to the ELISA plate by the end-user using a single set of conditions. This assumption may be false and therefore antigens and allergens not able to bind well to the plate under the conditions used will not be detectable or at best sub-optimally detectable.

There is therefore a need for an improved latex allergen assay. In order to produce such an assay antibodies against the individual latex allergens must be developed and be made available. In order to do that, the specific latex allergens must first be identified.

There have been many publications reporting on the occurrence of various latex allergenic proteins. Practically all the references to latex allergens characterise the proteins by molecular weight and/or occasionally by their isoelectric point. Latex allergens characterised by molecular weight or isoelectric point alone cannot be regarded as having been identified because:—

(a) Proteins break down during the manufacture of latex products and a single allergenic protein can hence appear as several proteins of lower molecular weights in a protein separation procedure such as gel filtration, HPLC, isoelectric focussing or electrophoresis to determine molecular weight or isoelectric point.

(b) Proteins may aggregate to form protein complexes that have different apparent molecular weights and isoelectric points from those of unaggregated proteins. and (c) Several different proteins may have similar characteristics (e.g. molecular weight) and cannot therefore be easily distinguished from one another.

According to the findings of the inventors of the present invention, these difficulties are overcome by:—

(i) Isolating specific latex allergenic proteins from natural rubber latex.

(ii) Developing monoclonal antibodies against those specific allergenic proteins to tag them and identify their breakdown protein fragments and sub-units.

According to the present invention, three specific latex allergens have been identified. The allergens have been designated Hev b IV, Hev b II and Hev b III in accordance with the allergen nomenclature system approved by the International Union of Immunological Societies and published in the Bulletin of the World Health Organisation (Marsh et al., 1986; Marsh, 1987). The protein Hev b IV was originally designated Hev b I by the present inventors; but has been re-designated Hev b IV because Hev b I has previously been assigned by other workers to the latex protein known as Rubber Elongation Factor found on the surface of rubber particles. (Czuppon et al).

Monoclonal antibodies have been generated against all three allergens and, significantly, some of these monoclonal antibodies also recognise the breakdown products or sub-units of the allergens. Assays are also provided according to the present invention and which are based on the interaction between the aforesaid specific allergenic proteins isolated from natural rubber latex and monoclonal antibodies developed against those proteins.

More specifically, the present invention provides an allergenic protein of natural rubber latex (designated Hev b IV) characterised by being in a substantially purified form and which is oligomeric and consists of three major species of monomeric polypeptides with molecular weights 50, 55 and 57 kDa that are disulphide-linked into dimers of approximate molecular weights 100, 110 and 115 kDa, and allergenic sub-units or aggregates thereof.

The invention further provides a second allergenic protein of natural rubber latex (designated Hev b II) characterised by being in a substantially purified form and which is composed of two polypeptide claims of molecular weights $^{34}/_{35}$ kDa and $^{36}/_{37}$ kDa, and allergenic sub-units or aggregates thereof.

The invention still further provides a third allergenic protein of natural rubber latex (designated Hev b III) characterised by being in a substantially purified form and which has a molecular weight of 24 kDa, and allergenic sub-units or aggregates thereof.

In another aspect, the invention provides monoclonal antibodies developed against the aforesaid allergens Hev b IV, Hev b II and Hev b III.

The invention further provides a method for the production of the aforesaid allergenic proteins Hev b IV, Hev b II and Hev b III.

In a still further aspect the invention provides assays for the qualitative and quantitative determination of the levels of allergens of natural rubber latex which are based on the interactions between specific protein allergens isolated from natural rubber latex or other tissue of the rubber tree *Hevea brasiliensis* and monoclonal antibodies developed against those allergens. The allergens being assayed may be present in the latex intended for use in the manufacture of latex products or they may be present in manufactured latex products. The assays can also be used to quantitate allergenic latex proteins in products made from dry rubber.

The invention further provides for the application of some or all of the same antibody-allergen interactions to identify and/or quantitate antibodies that mediate the occurrence of an allergic reaction induced by natural rubber latex. Such antibodies belonging to the class of antibodies known as IgE are normally found in blood or blood products.

In yet another embodiment of the invention, latex allergenic proteins and/or monoclonal antibodies against such proteins and/or a mixture thereof are labelled, for example with biotin, in order that their presence can be detected when they are used in an assay.

The invention provides also for the use of the aforesaid allergens Hev b IV, Hev b II and Hev b III, in in vivo or in vitro (ex vivo) diagnostic tests for the determination of Type I hypersensitivity to natural rubber latex (for example, the skin prick test or the histamine release test).

The invention also provides for the use of the aforesaid allergens, Hev b IV, Hev b II and Hev b III, as de-sensitising agents in the treatment of latex protein allergy.

Another embodiment of the invention provides for the leaching or washing of a latex product in a solution of salt (e.g. sodium chloride) or other solution with ionic strength greater than that of water to selectively remove latex allergens known to be soluble in solutions of ionic strength higher than that of water.

The inventors believe that they are the first to establish clearly the identities and properties of the three latex proteins, the first to report a reproducible method for their purification in large quantities from fresh latex and the first to demonstrate the allergenic nature of these proteins and to propose their use in assays. They have also developed monoclonal antibodies against these proteins. It is believed that Hev b II was completely unknown before the present invention. While the existence of Hev b III and Hev b IV had already been suggested, they were identified only to the level of their molecular weight or isoelectric point. Theoretically, proteins can be extracted from latex on the basis of their molecular weight even without knowing which component of latex the proteins originate from and without any other information. In practice, however, it is not easy to extract and purify specific proteins based on molecular weight alone with any reasonable assurance of the absence of contamination by proteins with similar characteristics (i.e. molecular weight) that co-purify with the desired allergenic proteins. As will be appreciated, this would make it difficult to aliquot out the precise quantities of pure allergens that would be required for quantitative immunological assays.

Results from experiments carried out suggest that the three specific allergenic proteins identified by the present inventors, designated Hev b IV, Hev b II and Hev b III, and their breakdown products or sub-units, account for a very large proportion of the latex protein allergens that have previously been reported.

Monoclonal antibodies are very specific for the particular allergens and antigenic sites (epitopes) that they recognise. Using an appropriate monoclonal antibody that recognises an epitopic site that is present in the breakdown fragments and sub-units of the parental allergen, the identities of such fragments and sub-units can be elucidated.

Besides their importance in identifying protein allergens and their breakdown fragments and sub-units, the monoclonal antibodies are also important for the purpose of developing commercial allergen assays in that (as compared with polyclonal antibodies) they lend themselves to sustained production in a consistent form and on the scale required for commercialisation.

Yet a further advantage of monoclonal antibodies is that they can be incorporated into a system of protein purification known as "affinity chromatography". Using such a system, the allergens that the monoclonal antibodies recognise can be isolated and purified in relatively large quantities, sufficient for their use in one variation of the allergen assay, known as a "competitive binding assay", in which both the antibodies and antigens are required. Pure allergens may also be used in immunological assays to quantitate the latex-induced antibodies (IgE) in a blood sample, or for use in skin prick tests for diagnostic purposes.

According to the present invention, selected monoclonal antibodies developed against the allergens Hev b IV, Hev b II and/or Hev b III are used in the development of immunoassays for the quantitation of allergens or the quantitation of latex specific IgE. Three monoclonal antibodies that recognise the latex allergens Hev b II, Hev b III and Hev b IV are USM/RB4, USM/RC2 and USM/RB3 respectively.

Immunoassays that incorporate the use of specific allergens are superior to immunoassays where the allergens are contained in unfractionated latex serum. In the latter, the exact allergen level in the serum is unknown while the consistency of the allergen in latex sera from different sources is also uncertain.

Further, immunoassays that incorporate the use of monoclonal antibodies specific for allergens are superior to those using polyclonal antibodies in immunoassays where whole latex sera, allergen-enriched or semi-purified antigen preparations are used instead of purified specific allergens.

Examples of immunoassays which form part of this invention are:—
(a) A competitive binding assay in which the test sample is used to inhibit binding of labelled specific allergens to a solid phase bearing either a monoclonal antibody or antibodies, or a polyclonal antiserum or antibodies.
(b) A two-site assay in which polyclonal antibodies bound to a solid phase are used to "capture" specific allergen(s) and the presence of the captured allergen detected by a monoclonal antibody which may or may not be labelled directly.
(c) A two site-assay in which monoclonal antibodies bound to a solid phase are used to "capture" specific allergen(s) and the presence of the captured allergen detected by a polyclonal antibody which may or may not be labelled directly.
(d) A two-site assay in which monoclonal antibodies bound to a solid phase are used to "capture" specific allergen(s) and the presence of the captured allergen detected by other monoclonal antibodies which may or may not be labelled directly.
(e) Any form of immunoassay in which the specific allergens Hev b Iv, Hev b II and Hev b III are used bound or in solution as in nephelometry, radioallergosorbant assays (RAST) or RAST inhibition assays.

The various aspects of the present invention will now be described in more detail and with reference to the accompanying drawings, wherein:—

FIG. 1: Sequential fractions obtained by Sephadex G-150 gel filtration of C-serum. The major peaks, A, B and C are indicated. Peak A represents the void volume that contains mainly small rubber particles (approx. 45 nm diameter) and large proteins greater than 300,000 kDa molecular weight.

Figure 2:
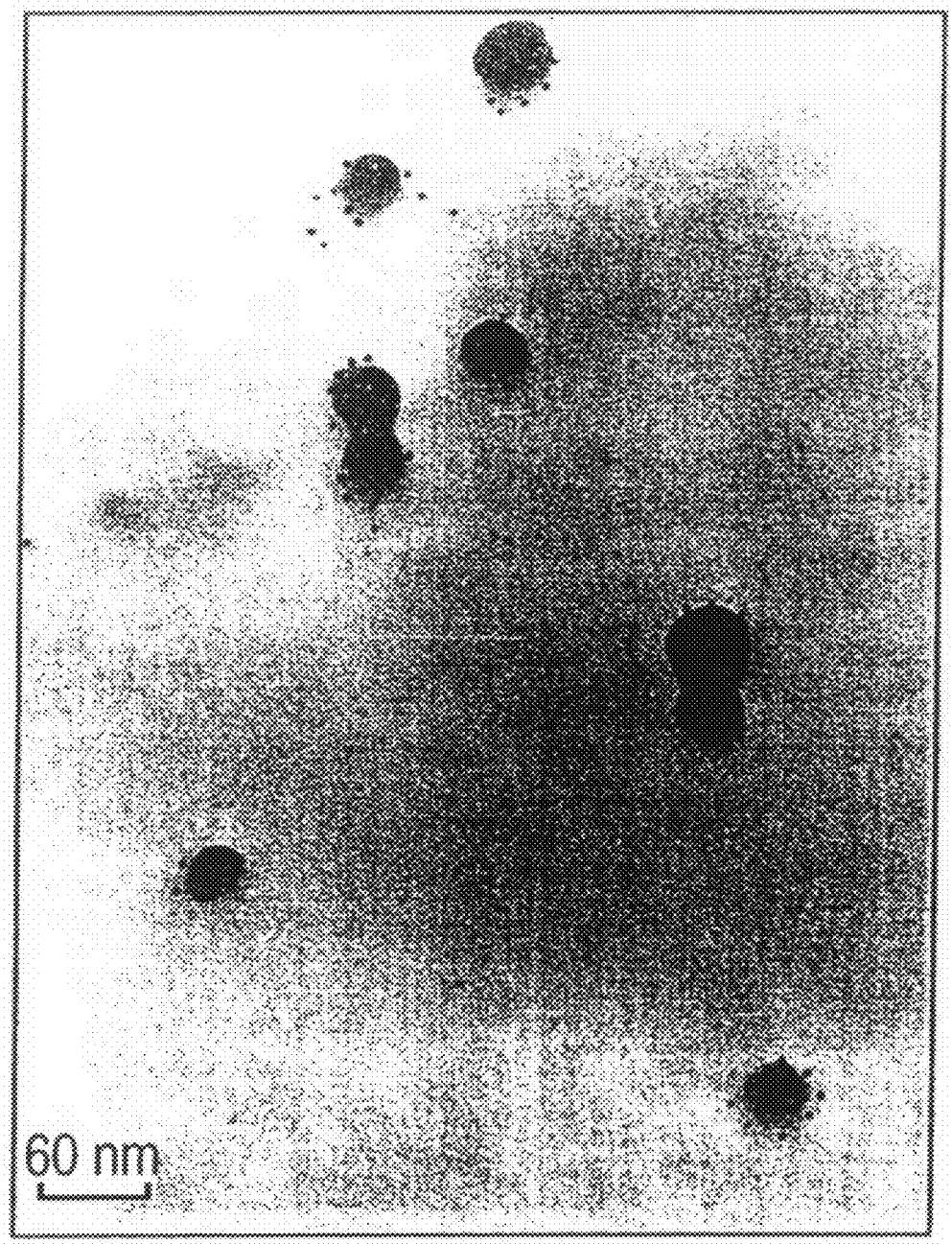

FIG. 2: Immuno-gold detection of Hev b III on the surface of small rubber particles fractionated from the C-serum. Gold particles conjugated to goat anti-mouse IgG indicate the presence of the monoclonal antibody USM/RC2 which binds specifically to Hev b III.

Figures 3A, 3B, 3C:
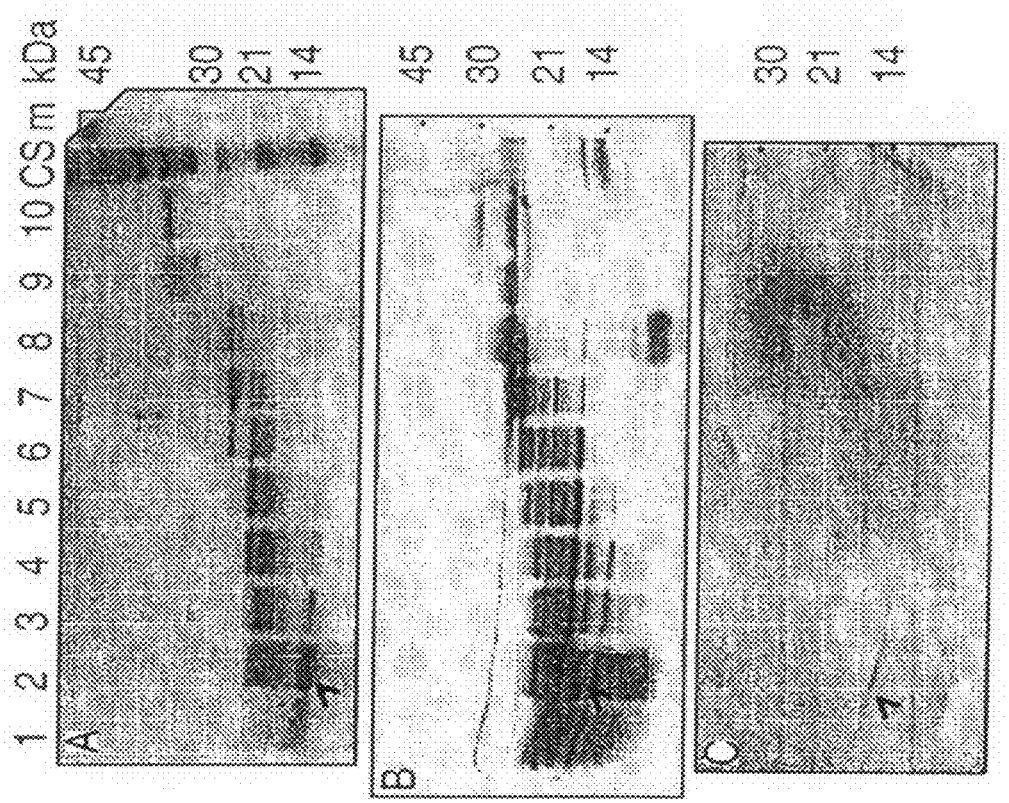

FIG. 3A-C: Preparative gel electrophoretic analysis of Hev b III. Western blot of sequential fractions of a mixture of B-serum and C-serum from a preparative electrophoretic cell. The protein fractions were subjected to SDS-polyacrylamide gel electrophoresis (15% gel) and stained with Coomassie Blue (FIG. 3A), incubated with the monoclonal antibody USM/RC2 (FIG. 3B) and incubated with patient plasma and tested for bound IgE—FIG. 3C. (CS-C-serum).

FIG. 3.1: Western blot of proteins extracted from the rubber cream of centrifuged latex and incubated with blood serum from latex-allergic adult patient (left) and from latex-allergic spina bifida patients (right). SDS-PAGE (15% gel). The Hev b III band is indicated by an arrow FIG. 4: Two-dimensional polyacrylamide gel electrophoresis of a mixture of B-serum and C-serum in the ratio 2:5. Isoelectric focussing was used in the first dimension and SDS-polyacrylamide gel electrophoresis was used in the second dimension. The gel was electro-blotted on to nitrocellulose membrane and incubated with the monoclonal antibody USM/RC2. A range of latex proteins (mainly of estimated pI 4.4 to 4.46 and with molecular weights of about 14 to 24 KDa) binds with USM/RC2.

Figure 5:
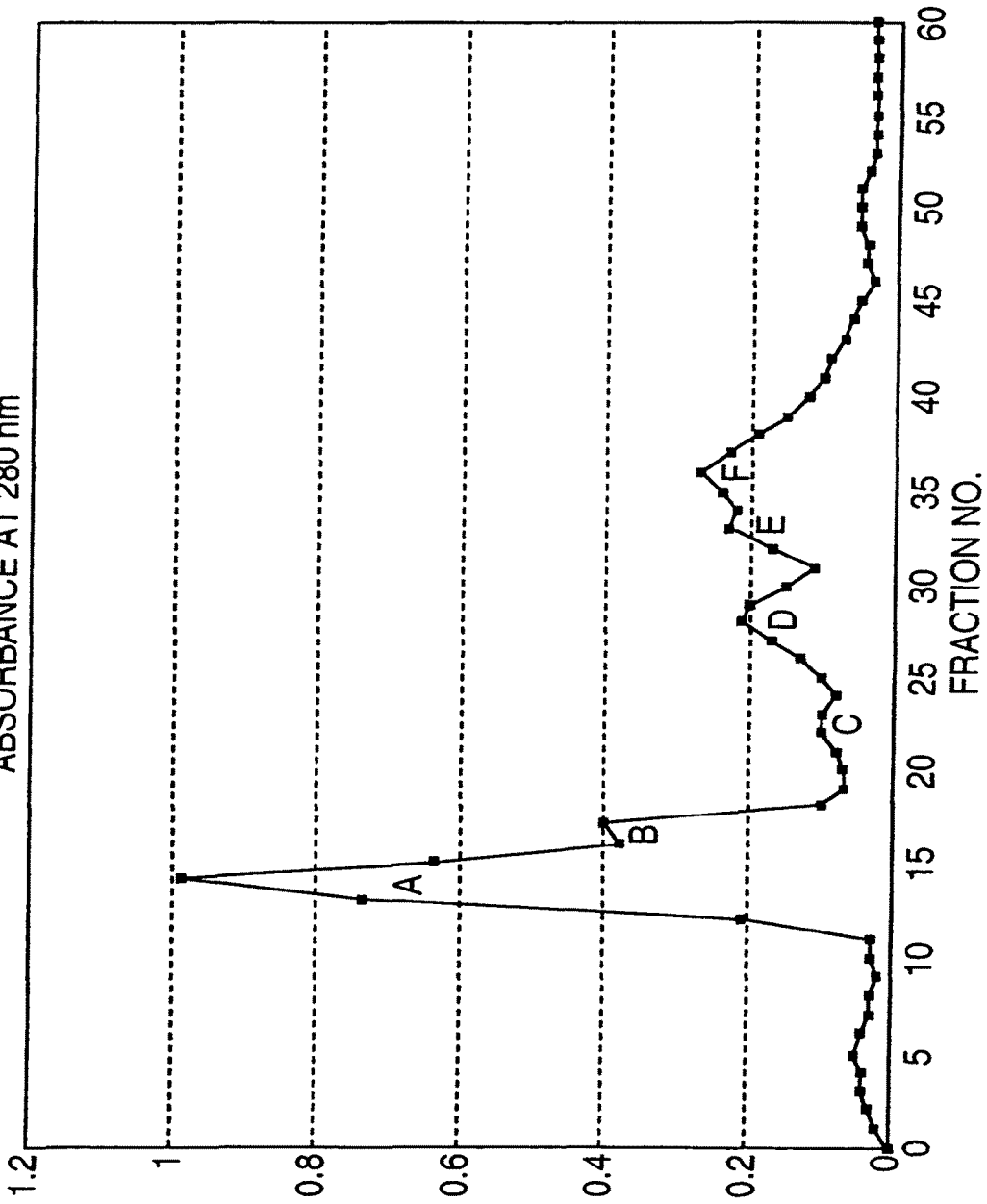

FIG. 5: Sequential protein fractions obtained by Sephacryl S200 gel filtration of the precipitate obtained from dialysed B-serum. The precipitate was re-dissolved in 0.35M sodium chloride solution before gel filtration. The main fractions A to F are indicated.

FIGS. 6A and B: Electrophoretic separation (15% gel) of proteins obtained from Sephacryl S200 gel filtration. Lane 1: Peaks E and F combined; Lane 2: Peaks A and B combined; Lane 3: Molecular weight markers. FIG. 6A: Gel stained with Coomassie Blue. FIG. 6B: Western blot of gel incubated with plasma for a patient allergic to latex.

FIGS. 7A-C: Purification of Hev b IV by gel filtration chromatography. The proteins in the various peaks were separated by SDS-polyacrylamide gel electrophoresis (15% gel). The gel was stained in Coomassie Blue (a)—FIG. 7A. A matching Western blot was probed with homotypic antiserum against Hev b IV (b and c). The test samples were reduced and heated (b)—FIG. 7B or unreduced and unheated (c)—FIG. 7C. (M—Molecular weight markers, BS—B-serum).

FIGS. 8A and B: Western blots of latex proteins probed with homotypic antiserum to allergen Hev b IV (A)—FIG. 8A and the monoclonal antibody (USM/RB3) to Hev b IV—FIG. 8B. Lane 1: B-serum, Lane 2: B-serum+C-serum. Lane 3: C-serum. All samples were run under non-reducing conditions without heat.

Figure 9A:
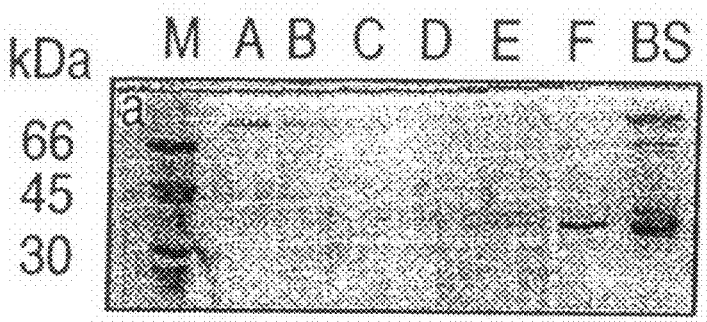
Figure 9B:
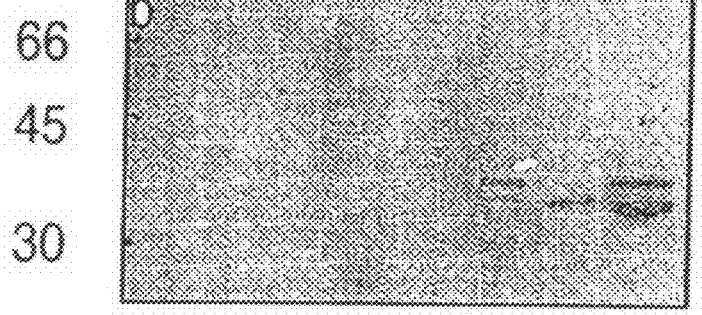

FIGS. 9A and B: Purification of Hev b II by gel filtration chromatography. The proteins in the various peaks were separated by SDS-polyacrylamide gel electrophoresis (15% gel). The gel was stained in Coomassie Blue (a)—FIG. 9A. A matching Western blot was probed with the monoclonal antibody USM/RB4 (b)—FIG. 9B. (M—Molecular weight markers, BS =B-serum).

Figure 10A:
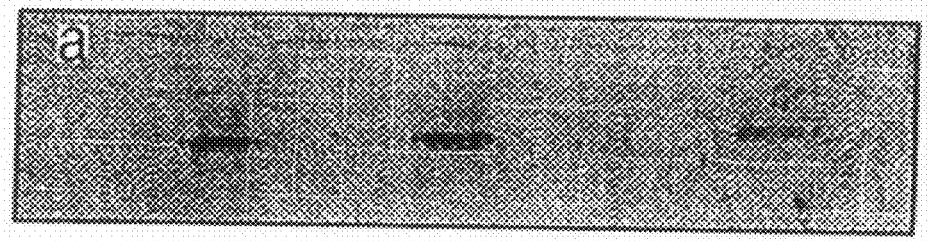

FIG. 10: Panel a—FIG. 10A: Preparative gel electrophoretic analysis of allergen Hev b IV. B-serum was separated under non-reducing and non-denaturing conditions using a 7.5% gel. Incubated with the monoclonal antibody USM/RB3.

Figure 10B:
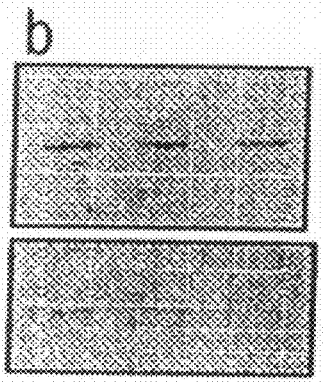

Panel b—FIG. 10B: Western blots of purified Hev b IV. Incubated with the monoclonal antibody USM/RB3 (top) with plasma of a patient allergic to latex (bottom). SDS-polyacrylamide gel electrophoresis was run on a 12% gel.

Figure 10C:
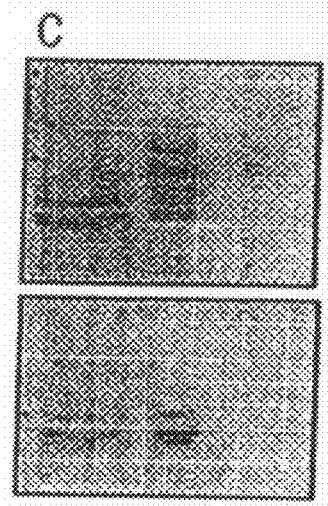

Panel c—FIG. 10C: Western blots of purified Hev b II. Incubated with plasma of a patient allergic to latex (top) and with the monoclonal antibody USM/RB4 (bottom). SDS-polyacrylamide gel electrophoresis was run on a 12% gel.

Figure 11:
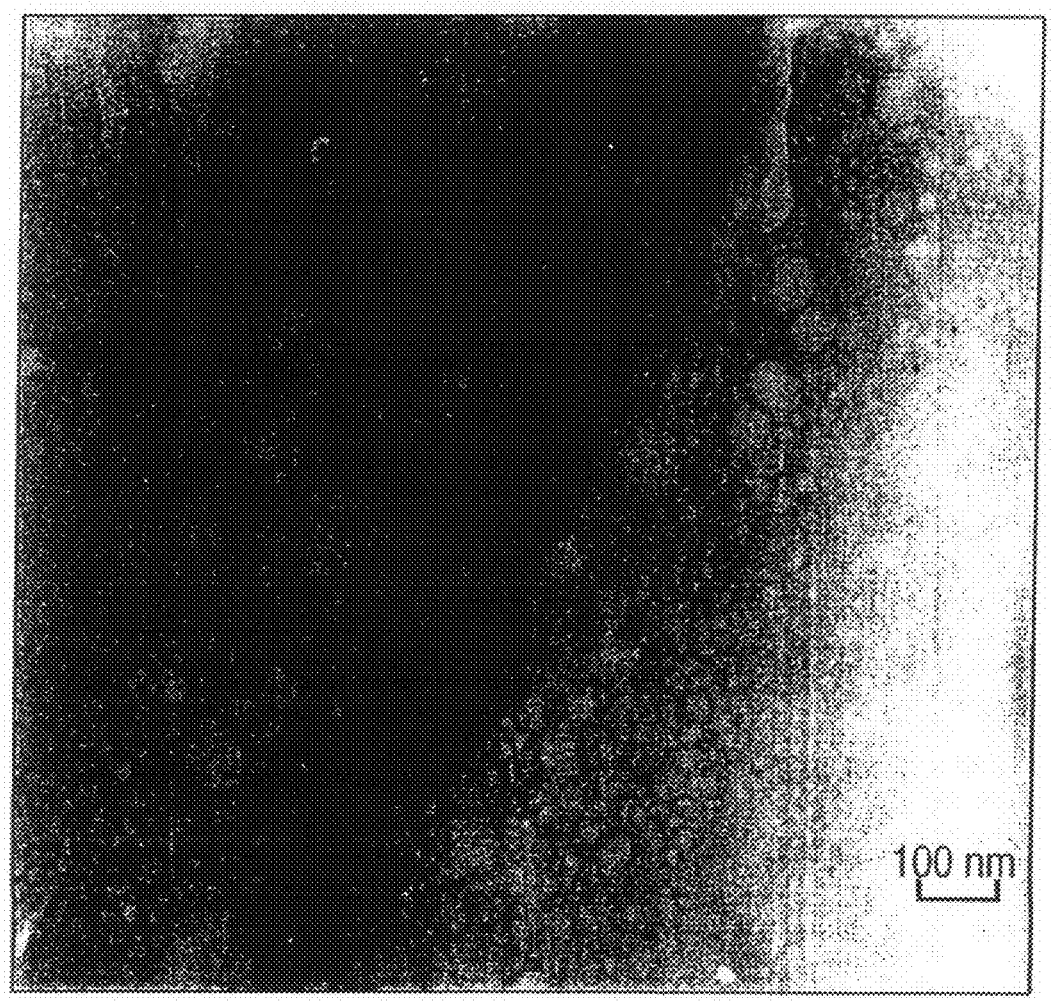

FIG. 11: Immuno-gold detection of Hev b IV on the microhelices (shown occurring in bundles) prepared from B-serum. Gold particles conjugated to goat anti-mouse IgG indicate the presence of the monoclonal antibody USM/RB3 which binds specifically to Hev b IV.

Figure 12:
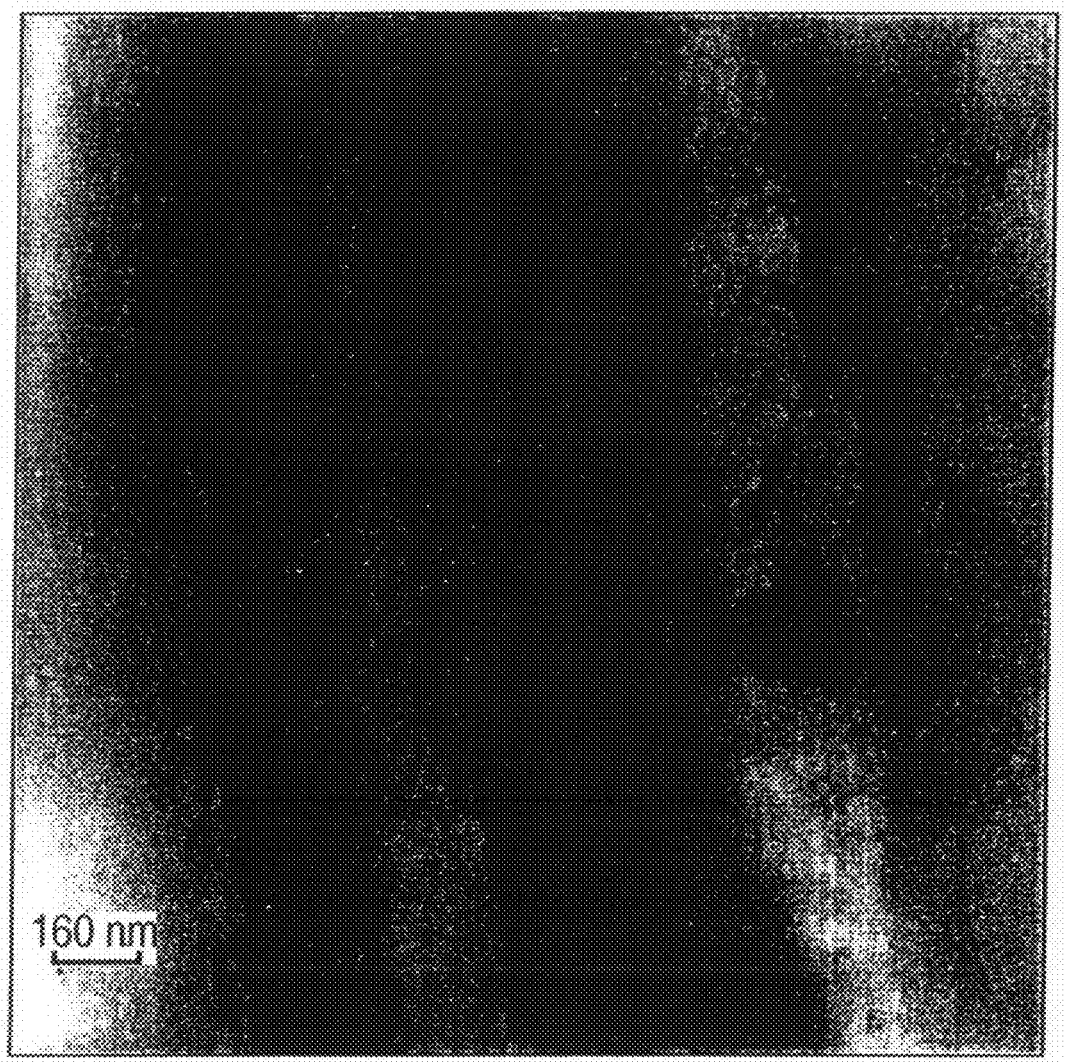

FIG. 12: Recognition of microhelices by IgE from blood plasma of a patient allergic to Hev b IV (but not to Hev b II) from natural rubber latex. Microhelices were incubated with blood plasma and then with a monoclonal anti-human IgE antibody. Labelling was subsequently carried out with goat anti-mouse antibody conjugated to 10 nm colloidal gold.

Figure 13:

FIG. 13: Immuno-gold detection of polyclonal antibodies against latex glove proteins. The antibodies were raised in rabbits. Gold particles conjugated to goat anti-rabbit IgG indicate the presence of immunogenic polypeptides on the microhelices (shown occurring in bundles) prepared from B-serum.

Figure 14A:
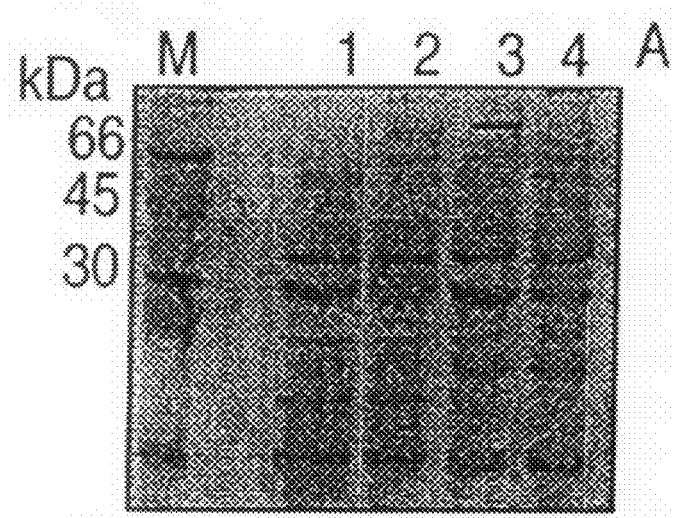

FIGS. 14A and B: SDS-PAGE (15% gel) separation of B-serum subjected to different treatments. A corresponding Western blot was probed with polyclonal homotypic antiserum against Hev b IV-F*ig.* 14B.

Prior to electrophoretic separation, the B-serum samples were reduced and heated (Lane 1), reduced and unheated (Lane 2), unreduced and heated (Lane 3) and unreduced and unheated (Lane 4). The gels were stained in Coomassie Blue—FIG. 14A.

M=Molecular weight markers

Figure 15A:
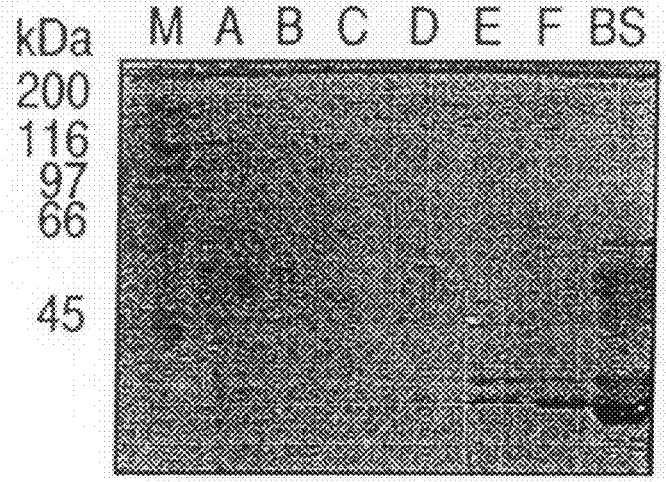
Figure 15B:
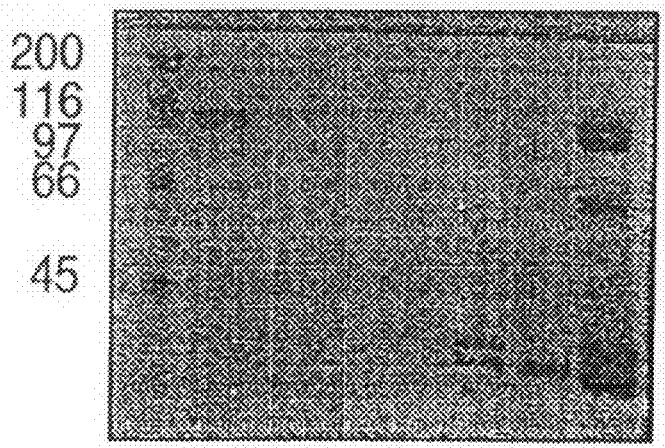

FIGS. 15A and B: SDS-PAGE (10% gel) of fractionated proteins (Fractions A to F as described in the text) derived from the precipitation of B-serum by dialysis. Prior to electrophoretic separation, the samples were reduced and heated (top panel) FIG. 15A and unreduced and heated (bottom panel) FIG. 15B. The gels were stained in Coomassie Blue.

M=Molecular weight markers; BS=B-serum.

Figure 16:
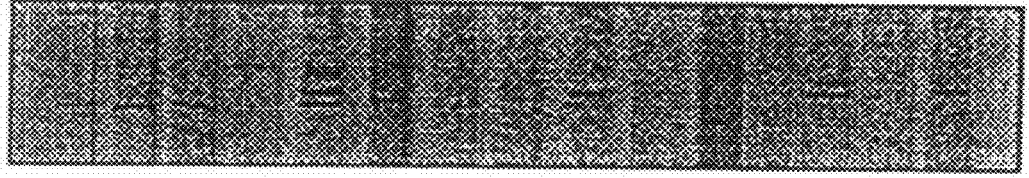

FIG. 16: Western blot strips of Hev b II probed with the monoclonal antibody USM/RB3 (Lane 14), USM/RB4 (Lane 15) and IgE from allergenic patients (Lanes 1 to 13).

Figure 17A:
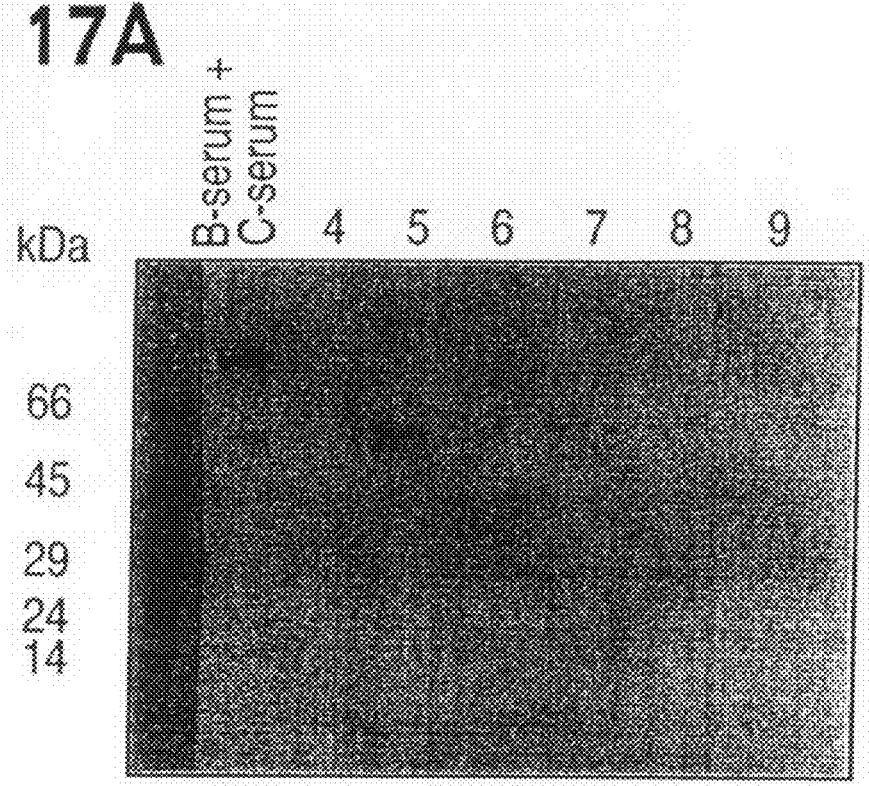
Figure 17B:
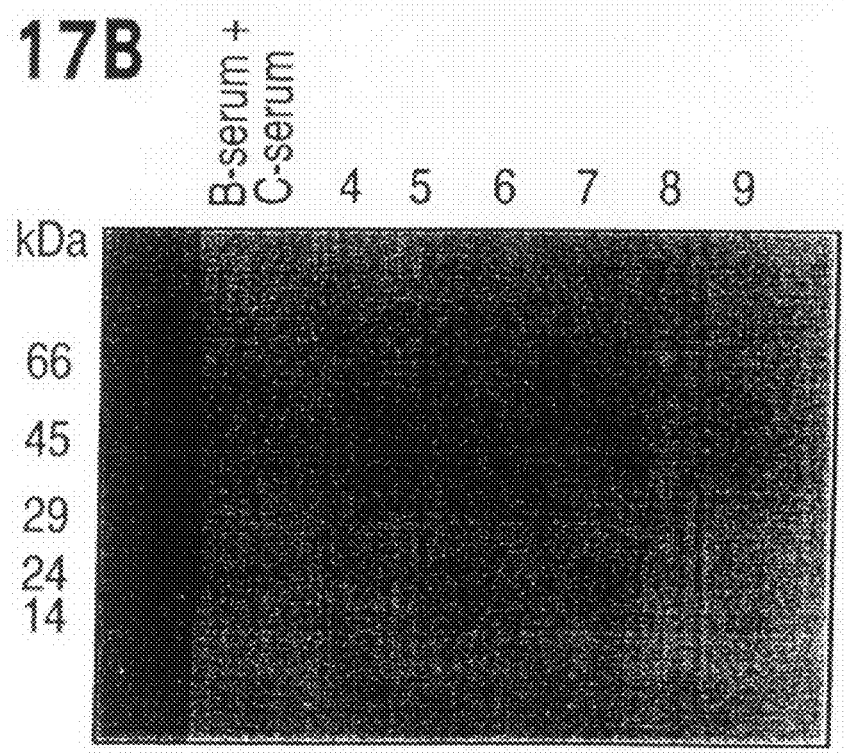

FIGS. 17A and B: Western blots of electrophoretic separation (15% gel) of protein eluates from six brands of gloves (labelled 4-9). Polyacrylamide gel electrophoresis was carried out under reducing and denaturing conditions. The blotted nitrocellulose membrane was incubated with homotypic antiserum to the allergen Hev b IV (Blot A) FIG. 17A and with the monoclonal antibody USM/RB4 which is specific for the allergen Hev b II (Blot B) FIG. 17B.

Mouse antiserum directed against B-serum was produced by immunising Balb/c strain mice with 0.5 ml B-serum intraperitoneally, followed by a second dose three weeks later. The mice were bled by cardiac puncture two weeks after the second dose and the serum separated was stored frozen in aliquots. The serum was found to be homotypic for the protein Hev b IV by Western blot analysis.

Monoclonal antibodies against latex proteins were than generated. Spleen cells from Balb/c mice immunised with latex proteins from the rubber tree *Hevea brasiliensis* were fused with mouse myeloma cells following protocols previously described by Kohler and Milstein (1975, 1976). The resulting hybridoma cells were screened for antibodies specific to latex proteins using several immunoassays. Selected hybridomas were recloned twice and monoclonal antibodies secreted were used either in unpurified form in hybridoma cell supernatants or as preparations purified by affinity chromatography. Samples of the hybridoma cell lines that secrete the monoclonal antibodies USM/RB4, USM/RC2 and USM/RB3 which recognise the latex allergens Hev b II, Hev b III and Hev b IV respectively have been deposited at the European Collection of Animal Cell Cultures, Centre for Applied Microbiology & Research, Salisbury, Wiltshire, United Kingdom, in its capacity as an International Depository Authority. The cell line for USM/RB4 has been assigned the accession number 94120727 deposited on 7 Dec. 1994. The cell lines for USM/RB3 and USM/RC2 have been assigned the following provisional accession numbers:

|  | Accession No. | Deposit Date |
| --- | --- | --- |
| USM/RB3 | 94120726 | 7 Dec. 1994 |
| USM/RC2 | 94120728 | 7 Dec. 1994 |

Proteins were next extracted from latex of the rubber tree, *Hevea brasiliensis*, and specific allergens identified. Monoclonal and homotypic antibodies against these proteins were used to identify particular proteins and their molecular weights determined. Allergenic proteins were identified by determining those proteins which are recognised by IgE antibodies in the blood plasma obtained from patients known to be allergic to latex. The allergens identified in this manner were cross matched with proteins identified by monoclonal and homotypic antibodies.

The allergens identified were then purified by several conventional methods and the identity of the proteins purified confirmed by tagging with monoclonal and homotypic antibodies. The isoelectric points (pI) of the purified allergens were determined using the LKB Multiphor Model 2117 electrofocusing apparatus equipped with precast Ampholine PAG-plate of pH range 3.5 to 9.5 following the manufacturer's instructions (Pharmacia LKB, Sweden). About 15 µl of test sample concentrated in 1% glycine was applied to the polyacrylamide gel. The fractionation and purification of the three latex allergens, designated Hev b IV, Hev b II and Hev b III, is now described.

Upon high speed centrifugation, latex separates into three main fractions: the rubber cream at the top, the "bottom fraction" and the C-serum in between. Hev b III is located on the surface of the small rubber particles (average size about 100 nm diameter). Many of these particles, particularly those smaller than average size, do not separate out with the rubber cream during centrifugation and so remain in the C-serum.

As C-serum is the aqueous phase of latex that is obtained when latex is centrifuged, C-serum proteins are generally water-soluble. Nevertheless, C-serum is by no means a homogenous fluid, but contains small quantities of mainly minute insoluble materials that are not separated by the latex centrifugation process. Forming the bulk of these insoluble materials are very small rubber particles, their presence having been confirmed by electron microscopy. As Hev b III is found on the surface of these small rubber particles that are suspended in C-serum, it is technically a C-serum protein. It is, however, not one of the soluble proteins that are normally associated with C-serum. Hev b III can be solubilised by detergents and is partly solubilised by ammonia.

To extract Hev b III, latex was collected from the tapped rubber tree in a chilled container. The latex was centrifuged in a Sorvall RC 5C high speed centrifuge at 19,000 r.p.m. (43,000 g) for 2 hours and the small rubber particles, which are located in "Zone 2" of centrifuged latex (Moir, 1959) were recovered from the centrifuge tube. The Zone 2 rubber cream is re-suspended in a solution of 30% sucrose to wash away contaminating C-serum and the suspension was then re-centrifuged. The rubber cream was treated with a mixture of 0.01% Triton X-100 and 1% sodium dodecyl sulphate (SDS) to extract the membrane proteins.

The Zone 2 rubber extract was subjected to SDS-polyacrylamide gel electrophoresis (SDS PAGE) to determine its molecular weight. There are two main proteins in the Zone 2 rubber extract electropherogram detectable by Coomassie Blue staining: a small amount of protein of approximately 14 kDa and a larger amount of protein of 24 kDa which is Hev b III. Notwithstanding the apparent molecular weight of 24 kDa for Hev b III as determined by standard molecular weight markers in conjunction with SDS-polyacrylamide gel electrophoresis, mass spectrometry of the protein shows various species of molecular weights, 22.258, 22.533, 22.790 and 23.058 kDa. The value of 24 kDa will nevertheless be used in subsequent references to the molecular weight of Hev b III in this document. Tryptic digestion of Hev b III revealed the following internal amino acid sequences:

```
                                              (SEQ ID NO: 1)
Val Ser Ser Tyr Leu Pro Leu Leu Pro Thr Glu Lys
1               5                   10;

(SEQ ID NO: 2)
Gly Asp Leu Ser Thr Val Ser Arg Leu Lys
1               5                   10;

(SEQ ID NO: 3)
Ile Val Leu Asp Val Ala Ser Ser Val Phe Asn Thr
1               5                   10

Arg Lys Gln Glu Lys Gln Lys;
            15

(SEQ ID NO: 4)
Val Thr Pro Val Tyr Tyr Leu Gly Thr Pro Thr Val
1               5                   10;
```

A monoclonal antibody, USM/RC2, has been developed which recognises (reacts specifically with) Hev b III and polypeptide fragments derived from degradation of Hev b III.

Alternatively, Hev b III can be prepared by passing C-serum through a Sephadex G-150 chromatography column (2.6 cm×81 cm) with 0.25M Tris-HCl of pH 8.0 as the eluting buffer. The fractionation of C-serum is followed by monitoring the absorbance of the eluted fractions at 280 nm. The first major peak that is eluted represents the void volume of the column and contains considerable quantities of small rubber particles (Peak A, FIG. 1). This fraction is dialysed, concentrated by freeze-drying and extracted with a mixture of 0.01% Triton X-100 and 1% sodium dodecyl sulphate (SDS).

The immuno-gold labelling technique was used to demonstrate that the protein which USM/RC2 recognises is on the surface of small rubber particles suspended in C-serum. Small rubber particles (about 45 nm diameter) obtained from the void volume of gel-filtered C-serum were fixed briefly in osmium tetroxide and deposited on to formvar-carbon coated nickel grids. The grids were first blocked for 30 minutes with phosphate buffered saline, pH 7.2 containing 1% bovine serum albumin (PBS-BSA) and incubation was carried out with USM/RC2 for 15 minutes. After rinsing, incubation was carried out for a further 15 minutes with 5 nm goat anti-mouse immunoglobulin (IgG) gold conjugate, contrasted with negative stain 2% phosphotungstic acid (pH 6.8). Upon examination under the electron microscope, gold particles were observed on the surface of the small rubber particles (FIG. 2), indicating that the polypeptide that USM/RC2 recognises (Hev b III) is on the surface of the small rubber particles which are suspended in C-serum.

The parental allergen, Hev b III, is susceptible to degradation into smaller polypeptide fragments. This degradation is enhanced by the presence of "B-serum" which is the liquid phase extracted from the bottom fraction (see below for description of the method to prepare B-serum).

When C-serum and B-serum are mixed together in the ratio 5:2, the protein bands from the Western blots of incubated with the monoclonal antibody USM/RC2 are not derived from B-serum since they are not picked up by USM/RC2 in the absence of C-serum. Additionally, in the Sephadex column filtration of C-serum (see above), the early-eluted fractions (the void volume containing rubber particles) react strongly with USM/RC2 (Peak A, FIG. 1). On the other hand, the medium and late-eluted fractions (where soluble proteins are expected to be found) have much lower reaction with the monoclonal USM/RC2, indicating much less of Hev b III in these fractions (Peaks B and C, FIG. 1). These observations are consistent with the proposition that Hev b III is associated with the small rubber particles found in the early eluted fractions.

The array of polypeptides derived from Hev b III can be distinctly seen after separating C-serum proteins which have been treated with B-serum using preparative SDS PAGE whereby fractions containing the polypeptide components are recovered. The sequential fractions were subjected to SDS PAGE followed by transfer of the proteins on to a nitrocellulose membrane (Western blotting). The membrane was then incubated with the monoclonal antibody USM/RC2 and detection of this binding was achieved by using a secondary antibody conjugated with an enzyme (horseradish peroxidase) which on reaction with its substrate in the presence of 4-chloro-1-naphthol generates a coloured product.

In a variation of the above procedures to test for the presence of protein bands binding to monoclonal or homotypic antibodies, the nitrocellulose membrane was incubated in a solution containing serum or plasma of patients allergic to latex. Patients' IgE bound to proteins immobilised in the membrane can then be detected by using an enzyme conjugated secondary antibody with specificity for the epsilon heavy chain of human IgE. Bound antibody can then be visualised as described above using a colorigenic substrate. The Western blots indicate that many breakdown products of Hev b III, ranging from about molecular weights 5 kDa to 24 kDa are recognised by the monoclonal antibody USM/RC2 (FIG. 3, panels A and B). Proteins of molecular weight greater than 24 kDa are also observed, suggesting the possible occurrence of protein aggregation. The binding of USM/RC2 to the various polypeptides show unequivocally that they are of common origin from Hev b III. Of the proteins derived from Hev b III, at least one, of molecular weight 12 kDa, is allergenic by virtue of its binding with IgE from latex allergic patients (FIG. 3, panel C). A Western blot of Hev b III prepared from the rubber cream of centrifuged fresh *Hevea* latex was incubated with serum pooled from latex IgE-positive spina bifida patients. Binding of IgE to Hev b III indicated that the spina bifida patients were particularly allergic to this protein (FIG. 3.1).

The monoclonal antibody Hev b III was further characterised by two-dimensional (2-D) polyacrylamide gel electrophoresis of a mixture of B-serum and C-serum mixed in the ratio of 2:5. Isoelectric focussing was used in the first dimension and SDS-polyacrylamide gel electrophoresis was used in the second dimension. Silver staining reveals a number of proteins of different isoelectric points (pI) and molecular weights. A matching 2-D gel was electro-blotted on to a nitrocellulose membrane (Western blot) which was then incubated with the monoclonal antibody to Hev b III. The latex proteins binding to the antibody are revealed by an enzymic reaction using a secondary enzyme-conjugated antibody. The polypeptides that are bound specifically to Hev b III are found to be mainly of the molecular weights ranging from 14 to 24 kD with pI as shown in FIG. 4. The spatial distribution of these polypeptides on the Western blot are very similar to that for latex proteins to which patients suffering from spina bifida are allergic (Alenius, 1994).

To extract Hev b IV and Hev b II, latex was collected and centrifuged as described above. The bottom fraction was recovered from the centrifuged latex and B-serum was prepared by alternate freezing and thawing cycles to rupture the lutoids which are the main constituents of the bottom fraction (Hsia, 1958). The serum (B-serum) that is released from the ruptured lutoids was recovered by further centrifugation. B-serum in aliquots of 10 ml was dialysed against 2 litres of distilled water at approximately 5° C. The resulting precipitate, which was recovered by centrifugation at 20,000 g for 30 minutes, is re-dissolved in 10 ml of 0.35 M sodium chloride; the solution was kept in an ice water bath throughout this operation.

An alternative method to extract Hev b IV and Hev b II is to mix B-serum and C-serum in the ratio 2:5 and to allow precipitation of the allergens for 15 minutes to overnight at room temperature. The resulting precipitate is collected by centrifugation and is redissolved in 0.35 M sodium chloride or phosphate buffered saline.

The crude extract of Hev b IV and Hev b II was chromatographed on a column (70×1.6 cm) of Sephacryl S-200 equilibrated with 0.35 M sodium chloride and elution was carried out in the same solvent. Fractions of 5 ml were collected while optical densities of each fraction at 280 nm were measured. Several such column chromatography runs are made to recover substantial quantities of the components eluted from the column.

Fractions from six peaks, A to F, were recovered by the column chromatography described (FIG. 5). These fractions were tested by enzyme immunoassay to determine the presence of proteins recognised by a panel of monoclonal antibodies as well as for ability to bind IgE from latex allergic patients. These data are shown in Table I. A component or components of peaks A and B are recognised by 11 of 13 (84.6%) latex allergic patients while 4 of 13 (30.8%) recognise a component or components of peaks E and F.

TABLE I

BINDING OF PROTEINS IN FRACTIONS A TO F OBTAINED BY GEL COLUMN CHROMATOGRAPHY TO IgE IN PLASMA SAMPLES (a-m) AND TO MONOCLONAL ANTIBODIES USM/RB3 AND USM/RB4 (n and o).

| Antibody/antibody source | A | B | C | D | E | F |
|---|---|---|---|---|---|---|
| a. 9706 | ++ | ++ | + | + | | |
| b. 1012 | ++++ | ++++ | | | ++++ | ++++ |
| c. OB1 | ++ | ++ | + | + | | |
| d. A190 | ++++ | ++++ | | | +++ | +++ |
| e. 9586 | ++ | ++ | ++ | ++ | | |
| f. 3510-28 | ++ | ++ | | | | |
| g. ASP | + | + | | | | |
| h. 4414 | | | | | | |
| i. 4398 | ++ | ++ | | | +++ | +++ |
| j. 4376 | ++ | ++ | | | | |
| k. 4265 | ++ | ++ | | | | |
| l. 4396 | | | | | | |
| m. 4393 | +++ | ++ | | | + | + |

TABLE I-continued

BINDING OF PROTEINS IN FRACTIONS A TO F
OBTAINED BY GEL COLUMN CHROMATOGRAPHY TO IgE IN
PLASMA SAMPLES (a-m) AND TO MONOCLONAL
ANTIBODIES USM/RB3 AND USM/RB4 (n and o).

| Antibody/antibody source | A | B | C | D | E | F |
|---|---|---|---|---|---|---|
| n. USM/RB3 | ++++ | ++++ | + | w | + | + |
| o. USM/RB4 | + | + | w | w | ++++ | ++++ |

++++ = Strong protein-antibody binding
+ = Weak protein-antibody binding
w = Very weak protein-antibody binding Positive binding between protein and antibody was detected by an enzyme (peroxidase) reaction mediated by an enzyme-conjugated antibody against human IgE (for the patient plasma samples) and a secondary antibody against mouse immunoglobulin (for the monoclonal antibodies).

The monoclonal antibodies USM/RB3 and USM/RB4 distinguish between the components of peaks A and B and peaks E and F (Table I).

Proteins in Peaks A to F were separated by SDS-polyacrylamide gel electrophoresis where the sample was reduced with the addition of mercaptoethanol and heated. The main protein bands that were observed after Coomassie Blue staining are a major band of 50-57 kDa and minor bands of 65, 22 and 18 kDa from Peaks A and B and $^{36}/_{37}$, $^{34}/_{35}$ kDa from Peaks E and F (FIG. 6, Panel A). The $^{34}/_{35}$ kDa protein was more prominent than the $^{36}/_{37}$ kDa protein in Peak F, but they were generally found in similar amounts in Peak E. A matching gel was electro-blotted and then incubated with blood plasma known to contain latex-specific IgE. The proteins that are observed to be allergenic are those of molecular weights 48-58 kDa, 22 kDa and 65 kDa from Peaks A and B and $^{34}/_{35}$ and $^{36}/_{37}$ from Peaks E and F (FIG. 6, panel B).

Peaks A and B contain a high molecular weight protein when run under non-reducing conditions (FIG. 7, panel a) which is formed of disulphide-linked monomers of molecular weight ranging from 48 to 58 kDa consisting of 3 major species of polypeptide chains with apparent molecular weights 50, 55 and 57 kDa. These sub-units are all readily recognised by the homotypic antibody against Hev b IV (FIG. 7, panel b). However, when the acrylamide gel run under non-reducing conditions is electrophoretically transferred to nitrocellulose, it can be shown that this same homotypic antibody against Hev b IV now recognises range of smaller polypeptides with approximate molecular weights of 29 kDa, 32 kDa, 40 kDa, 50 kDa and 75-80 kDa. These polypeptides are also recognised by 10 other monoclonal antibodies (an example of which is USM/RB3) derived from different hybridoma clones, an example of one which is shown in FIG. 8.

β1,3 glucanase activity was detected in Peaks E and F by colorimetry. Samples from Peaks E and F were incubated with laminarin (1 mg ml$^{-1}$ in 50 mM sodium acetate buffer, pH 5.2). The release of reducing sugars indicated the presence of β1,3 glucanase activity. Peaks E and F contain the allergen Hev b II which exists as two polypeptide chains of molecular weights $^{34}/_{35}$ and $^{36}/_{37}$ kDa which are not linked by interchain disulphide bonds thus emerging from the gel filtration column at slightly different times. Both these polypeptides are recognised by two monoclonal antibodies, one of which is USM/RB4 (FIG. 9).

In a further characterisation of the allergenic proteins, B-serum was subjected to preparative gel electrophoresis where the sample was not reduced and not heated and sequential fractions collected as the proteins migrated through a 7.5% polyacrylamide gel. The content of these fractions were identified by using the monoclonal and homotypic antibodies described and both Hev b IV and Hev b II are recoverable in this manner. Hev b IV is recoverable as a high molecular weight protein under these conditions and is clearly separated into three major species which have apparent molecular weights of 100, 110 and 115 kDa respectively and these can be seen in lanes 2, 5 and 9 of FIG. 10a. When these fractions were subjected to SDS PAGE under reducing and denaturing conditions and transferred to nitrocellulose the resulting Western blots probed with homotypic antiserum to Hev b IV show a broad band with molecular weight range 48-58 kDa as previously described (see FIG. 7) thus proving that the single bands separated by preparative gel electrophoresis under the conditions described above represent a protein in peaks A and B which are recoverable by gel filtration. That this protein is also a human allergen is shown in FIG. 10b where the top panel represents a Western blot of the three fractions of Hev b IV recovered by preparative gel electrophoresis and the bottom panel shows IgE from latex allergic patients binding to the same three bands. Further evidence that this allergen Hev b IV contains 3 major species is shown by capillary electrophoresis (Beckman Instruments) on these samples which show 3 peaks. The same analysis shows that there are no other peaks observed in these samples, providing definitive evidence that the inventors have purified Hev b IV in its 3 major forms and that all these forms are recognised by IgE from latex allergic patients.

Being precipitated by dialysis and re-soluble in sodium chloride, Hev b IV and Hev b II behave similarly to a latex B-serum protein complex known as the microhelix (plural, microhelices). The microhelix is a glycoprotein complex of a filamentous helical structure that has been observed under the electron microscope and has been characterised in some detail previously (Archer et al., 1963; Gomez and Yip, 1975; Gomez and Tata, 1977; Tata and Gomez, 1980). As summarised by Gomez and Moir (1979), microhelices prepared from dialysed B-serum are 1 μm or more in length with a diameter of 20 nm, the fibre width is approximately 5 nm and the pitch of the helix, which is open and hollow, is about 30 nm. Individual microhelices are often associated into bundles (FIG. 11). At high resolution under the electron microscope, microhelices are seen to have a beaded structure consisting of spherical particles 3-3.5 nm in diameter, arranged in a helical manner with three to four particles per turn.

The technique of immuno-gold labelling was used to determine if either or both the proteins, Hev b IV or Hev b II, are components of the microhelix complex. Microhelices were prepared by dialysis of B-serum and were deposited on to formvar-carbon coated nickel grids. The grids were first blocked for 30 minutes with phosphate buffered saline, pH 7.2 containing 1% bovine serum albumin (PBS-BSA). Incubation for 15 minutes was carried out separately with the monoclonal antibodies USM/RB3 (which binds specifically with Hev b IV) and USM/RB4 (which binds specifically with Hev b II). These monoclonal antibodies serve as the primary antibodies in the immuno-reactions. After rinsing, the monoclonal antibodies that had successfully bound to the microhelices were detected by 15 minutes incubation with 10 nm goat anti-mouse immunoglobulin (IgG) gold conjugate (the secondary antibody), contrasted with negative stain 2% phosphotungstic acid (pH 6.8) and, examining under the electron microscope. As shown in FIG. 11, gold particles are concentrated on the microhelices that have been incubated with USM/RB3, indicating that the polypeptide that it recognises (Hev b IV) is a component of the microhelix complex. On the other hand, there is no association of gold particles with microhelices that have been incubated with USM/RB4, suggesting that Hev b II is probably not a component of the microhelix complex.

To further demonstrate that the microhelix is an allergen, the above immuno-gold labelling procedures were repeated, but with blood plasma from an allergic patient sensitive to Hev b IV but not to Hev b II used as the primary antibody source. The incubation pH was 8.0. A monoclonal antibody against IgE served as the secondary antibody of the immunoreaction while goat anti-mouse immunoglobulin (IgG) gold conjugate served as the tertiary antibody. As shown in FIG. 12, gold particles (5 nm) were observed to be associated with microhelices, indicating that the microhelix is an allergenic protein.

To confirm that the microhelix or its polypeptide derivatives are found in proteins extractable from latex gloves, aqueous latex glove eluate was prepared in phosphate buffered saline and injected subcutaneously into rabbits to raise polyclonal antibodies against the glove protein mixture (Sunderasan and Yeang, 1994). When immuno-gold labelling of the microhelix was carried out using these polyclonal antibodies, 10 nm gold particles conjugated to goat anti-rabbit IgG were clearly seen associated with the microhelices (FIG. 13), indicating that polypeptide components of the microhelix protein complex occur in latex glove eluate.

Hev b IV exists as an oligomer which consists of monomeric polypeptides of approximate molecular weight 55 kDa (50, 55, 57 kDa) that are disulfide linked into dimers of approximate molecular weight 105 kDa (100, 110, 115 kDa) as described above. Isoelectric focusing revealed Hev b IV to be an acidic protein with pI in the region of pH 4.5. Its N-terminal amino acid sequence has been determined as

```
                                          (SEQ ID NO: 5)
Glu Leu Asp Glu Tyr Leu Phe Ser Phe Gly Asp Gly
1               5                   10

Leu Tyr Asp Ala
             15
```

Figure 14B:
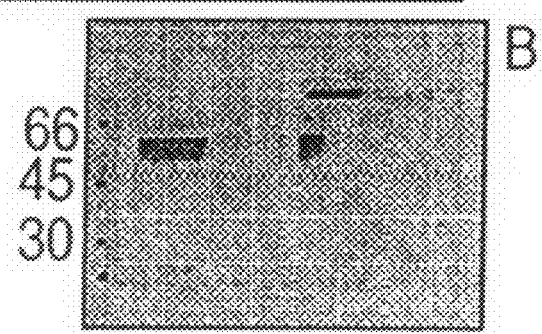

Gly Asn Ala. FIG. 14 shows a Coomassie Blue-stained SDS-PAGE gel with B-serum loaded in lanes 1-4. The B-serum samples were either reduced or not reduced, and heated at 95 C for 3 minutes or unheated before loading. A corresponding gel was electro-transferred to nitrocellulose membrane and the Western blot was probed with polyclonal antibodies homotypic to Hev b IV. The results show that Hev b IV exists as a broad band between about 50-57 kDa when the sample was reduced and heated (Lane 1). However, when the sample was heated but not reduced (Lane 3), Hev b IV is seen as a higher molecular weight band of about 105 kDa indicating that Hev b IV monomers (molecular weight 50-57 kDa) are disulfide-linked to form 105 kDa dimers. Further, when the sample was not heated nor reduced (Lane 4) the protein did not enter the gel giving only a very weak reactive band at 105 kDa suggesting that the 105 kDa dimers form larger oligomers which dissociate on heating.

The protein recovered in fractions A and S from the gel filtration procedure described above also contains a 50 to 57 kDa broad band which exists as a 100 to 115 kDa diner as shown in FIG. 15 where the top gel was run under reducing conditions while the bottom gel was run under non-reducing conditions to demonstrate the relationship between the 50 to 57 kDa and the 100 to 115 kDa bands.

Although the microhelix has been described before, as mentioned above, the results presented here represent the first report of its being immunogenic and allergenic. The polypeptide fragments of Hev b IV, that arise from protein denaturation or degradation, are described in detail in the present document.

The protein Hev b II was recovered in a different fraction and because the molecular weight is much smaller ($^{34}/_{35}$ and $^{36}/_{37}$ kDa) than Hev b IV, both polypeptide chains were recovered in the same fraction with the Coomasie Blue stained SDS PAGE gel showing no other visible bands. When this fraction was subjected to Western blot analysis after electrotransfer from an SDS-PAGE gel run under non-reducing conditions, it was clearly shown that the protein recognised by the monoclonal antibody USM/RB4 is also recognised by IgE from latex allergic patients. An example of such a reaction is shown in FIG. 10c where the top panel represents IgE binding to at least 4 bands in fraction 15 (middle track) and 2 bands in the B-serum control (left track).

Isoelectric focusing of Hev b II revealed a single band at pI approximately 9.6.

Hev b II could be electrophoresed on a cathodic native PAGE system. The protein appeared as a single band by Coomassie Blue staining after the electrophoresis at acidic pH according to the method of Reisfeld et al. (1962). A similar gel was incubated with laminarin (1.5 mg ml$^1$) in 50 mM sodium acetate buffer, pH 5.2, for 3 h at 37° C. The gel was then placed in a solution of 150 mM $K_2HPO_4$, pH 8.6, containing 0.05% aniline blue for 1 h (Cote et al., 1989). A stained band was observed corresponding to that seen after Coomassie Blue staining, indicating β1,3 glucanase activity. An internal peptide fragment of Hev b II showed an amino acid sequence:

```
                                          (SEQ ID NO:6)
Phe Asp Glu Asn Asn Xaa Gln Pro Glu Val Glu
1               5                       10;

and another peptide fragment showed the sequence:

SEQ ID NO:7)
Arg Asn Ile His Asp Ala Ile Arg Ser Ala Gly Leu
1               5                       10.

Gln
```

The former sequence showed 85.2% homology with the amino acids sequence for endo-1,3 β-glucanase present in the tobacco plant and the tomato plant.

A large amount of Hev b II in both molecular sizes can be obtained by detergent extraction of lutoid membranes. This suggests that Hev b II is associated with the lutoid membrane.

To further determine the importance of the proteins recognised by USM/RB4 as human allergens, Western blotting using nitrocellulose strips containing Hev b II protein in a reaction with IgE from latex allergic patients shows that 8 of 13 (61.5%) human blood plasma samples recognise Hev b II (FIG. 16). Purified Hev b II was used in this experiment and hence sensitivity of patients' IgE to it was greater in this instance than in the experiment depicted in Table I.

Should large amounts of Hev b IV, Hev b II or Hev b III be required (e.g. for the commercial preparation of immunoassays, they can be prepared by the methods described above. Alternatively, the monoclonal antibodies USM/RC2, USM/RB3 and USM/RB4 or their equivalent antibodies can be incorporated into "affinity chromatography" columns or other solid phase matrices. By reacting latex C-serum, B-serum or other latex derived preparations with such solid phase matrices and eluting with appropriate buffers, the respective allergens can be recovered in highly purified form.

The fact that Hev b IV and Hev b II are soluble in sodium chloride may be exploited in procedures to leach or wash latex products to remove allergenic proteins. Hev b IV and Hev b II (and their subunits and degradation products) are more effectively removed if a solution of salt (e.g. sodium chloride) or other solution with ionic strength greater than that of water is used in leaching or washing. An example of this effect is demonstrated in Table II which shows the extraction of total proteins, total antigens (i.e. allergens and non-allergens) and allergenic proteins binding to USM/RB4 by water and by 0.35M sodium chloride solution from a film of natural rubber latex. It is clear that while sodium chloride solution removes total protein and total antigens more effectively than water, the greater efficiency of sodium chloride is very much more marked in the case of latex allergens binding to USM/RB4 where only 4.5% of the extractable allergen is eluted in water as compared to 59.5 k of total protein and 77.7 k of total antigen extractable in water as compared to 0.35M sodium chloride. Hence, the use of 0.35M sodium chloride solution selectively increases the efficiency by which this particular latex allergen is extracted.

TABLE II

EXTRACTION OF TOTAL PROTEINS, TOTAL ANTIGENS AND ALLERGENS BINDING TO USM/RB4 BY WATER AND 0.35M SODIUM CHLORIDE SOLUTION.

|  | TOTAL PROTEINS (ug/ml) | TOTAL ANTIGENS (Arbitrary units) | ALLERGENS BINDING TO RB4 (Arbitrary units) |
| --- | --- | --- | --- |
| Eluted in water | 113.8 (59.5%) | 47.3 (77.7%) | 0.6 (4.5%) |
| Eluted in 0.35M sodium chloride | 191.3 | 60.9 | 13.4 |

Antigens and allergens were assayed by a competitive enzyme-linked immunosorbant assay (ELISA). Polyclonal antibodies raised in rabbits against latex gloves were used in the total antigen assay. Percentages are calculated taking the values obtained by sodium chloride elution as 100%.

EXAMPLE

This is an example of an assay according to the present invention in which monoclonal antibodies developed against specific allergenic proteins are employed to determine the level of those allergens in products (gloves) manufactured from latex.

As already mentioned, proteins eluted from commercial latex gloves have previously been used as the protein antigen component of immunoassays for the diagnosis of latex allergy or for the quantitation of latex allergens. A serious drawback of this approach is that different brands of gloves show qualitative and quantitative differences in their allergen composition, as can be seen from the findings presented in FIG. 17 and Table III below. USM/RB3 and USM/RB4 are monoclonal antibodies according to the present invention.

TABLE III

ALLERGENS FOUND IN GLOVE SAMPLES DO NOT CORRELATE WITH TOTAL PROTEIN CONCENTRATION.

| ANTIBODY/ SAMPLE | TOTAL PROTEIN (mg/ml) | USM/RB3 | USM/ RB4 | NEG CONT | HOMO- TYPIC ANTISERA |
| --- | --- | --- | --- | --- | --- |
| GLOVE 1 | 0.325 | 0.00 | 0.15 | 0.00 | 0.00 |
| GLOVE 2 | 0.324 | 0.30 | 0.51 | 0.02 | 1.8 |
| GLOVE 3 | 0.349 | 0.21 | 0.68 | 0.02 | 1.5 |
| GLOVE 4 | 0.143 | 0.20 | 0.08 | 0.02 | 1.00 |
| GLOVE 5 | 0.284 | 0.15 | 0.80 | 0.05 | 1.26 |
| GLOVE 6 | 0.261 | 0.12 | 0.18 | 0.02 | 1.83 |
| GLOVE 7 | 0.212 | 0.07 | 0.07 | 0.02 | 0.62 |
| GLOVE 8 | 0.177 | 0.19 | 0.06 | 0.02 | 0.77 |
| GLOVE 9 | 0.244 | 0.13 | 0.23 | 0.02 | 0.72 |
| B-SERUM | 0.024 | 6.39 | >9 | 0.04 | >9 |

REFERENCES

Alenius, H. (1994) Distribution of allergenic proteins between fractions of natural rubber latex separated by ultracentrifugation. Paper presented at the Workshop on Latex Protein Allergy, June 1994, Kuala Lumpur.

Archer, B. L., Barnard, D., Cockbain, E. G. Dickenson, P. B. and McMullen, A. I. (1963) Structure, composition and biochemistry of *Hevea* latex. The Chemistry and Physics of Rubber-Like Substances. Bateman, L. Ed. Maclaren & Sons Ltd., 43.

Axelsson, J. G. K., Johansson, S. G. O. and Wrangsjo, K. (1987) IgE-mediated anaphalactoid reactions to rubber. Allergy, 42, 46.

Beezhold, D. H. (1993) Measurement of latex protein by chemical and immunological methods. Paper presented at the Conf. on Latex protein allergy: the present position. Amsterdam.

Chevallier, M. H. (1988) Genetic variability of *Hevea brasiliensis* germplasm using isozyme markers. J. Nat. Rubb. Res., 3(1), 42.

Chrestin, H., Jacob, J. L. and d'Auzac, J. (19-85) Biochemical basis for cessation of latex flow and occurrence of physiological bark dryness. Proc. Int. Rubb. Conf. 1985 Kuala Lumpur, 3, 20.

Cohn, W. E. (1984) Methods Enzymol., 106, 1.

Cote, F., Letaqrte, J., Grenier, J., Trudel, J. and Asselin, A. (1989) Detection of β1,3 glucanase activity after native polyacrylamide gel electrophoresis: application to tobacco pathogenesis-related proteins. Electrophoresis, 10, 527.

Czuppon, A. B., Chen, Z., Rennert, S., Engelke, T., Meyer, H. E., Heber, M., Baur, X. (1993) The Rubber elongation factor of rubber trees (Hevea brasiliensis) is the major allergen in latex. J Allergy Clin. Immunol. 92, 690-7.

Gomez, J. B. and Moir, G. F. J. (1979) The Ultracytology of Latex Vessels in *Hevea brasiliensis*. M.R.R.D.B. Monograph No. 4, Malaysian Rubber Research and Development Board, 37.

Gomez, J. B. and Tata, S. J. (1977) Further studies on the occurrence and distribution of microhelices in clones of Hevea. J. Rubb. Res. Inst. Malaysia, 25(3) 120.

Gomez, J. B. and Yip, E. (1975) Microhelices in Hevea latex. J. Ultrastruct. Res., 52, 76.

Hsia, R. C. H. (1958) oxygen absorption by *Hevea brasiliensis* latex. Trans. Instn. Rubb. Ind., 34, 267.

Kohler and Milstein (1975) Continuous cultures of fused cells secreting antibody of predefined specificity. Nature, 256, 495.

Kohler and Milstein (1976) Derivation of specific antibody-producing tissue culture and tumour lines by cell fusion. Eur. J. Immunol., 6, 292.

Kurup, V. P., Kumar, A., Kelly, K. J. and Fink, J. N. (1993) Characterisation of a monoclonal antibody against latex protein associated with latex allergy. J. Allergy Clin. Immunol., 92(5), 638.

Lagier, F., Vervloet, D., Lhermet, I., Poyen, D. and Charpin, D. (1992) Prevalence of latex allergy in operating room nurses. J. Allergy Clin. Immunol., 90, 319.

Levy, D. A. (1993) Diagnosis of allergy to latex proteins. Paper presented at the Conf. on Latex protein allergy: the present position. Amsterdam.

Leynadier, F., Autegarden, J-E., Levy, D. A. (1993) Management of patients with latex protein allergy. Paper presented at the Conf. on Latex protein allergy: the present position. Amsterdam.

Leynadier, F., Pecquet, C. and Dry, J. (1989) Anaphalaxis to latex. Anaesthesia, 44, 547.

Marsh, D. G. (1987) The new International Union of Immunological Societies (IUIS) allergen nomenclature. J. Allergy Clin. Immunol., 80(5), 637.

Marsh, D. G., Goodfriend, L., King, T. P., Lowenstein, H. and Platts-Mills, T. A. E. (1986) Allergen nomenclature. Bull. WHO, 64, 767.

Moir, G. F. J. (1959) Ultracentrifugation and staining of Hevea latex. Nature, 184, 1626.

Nutter, A. F. (1979) Contact urticaria. Br. J. Derm., 101, 597.

Prematillake, S. P. and Yapa, P. A. J. (1985) A study of characterization of Hevea clones by serum protein patterns. J. Rubb. Res. Inst. Sri Lanka, 63, 25.

Prematillake, S. P., Yapa, P. A. J. and Bamunuarachi (1985) Serum protein patterns in healthy and brown bast affected trees of Hevea. J. Rubb. Res. Inst. Sri Lanka, 64, 7.

Reisfeld, R. A., Lewis, U. J. and Williams, D. E. (1962) Disk Electrophoresis of Basic Proteins and Peptides in Polyacrylamide Gels. Nature, London, 195, 281. Shamsul Bahri, A. R., Samsidar Hamzah, Hafsah Mohd. Ghazali and Yeang, H. Y. (1993) Latex allergy studies: Location of soluble proteins in latex examination gloves. J. Nat. Rubb. Res., 8(4), 299.

Slater, J. E. (1991) Latex antigens. Allergy and Clin. Immunol., 87(1), Pt. 2, Abs. 516.

Subramaniam, A. (1992). Reduction of extractable protein content in latex products. Proc. Int. Latex Conf.: Sensitivity to latex in medical devices., Baltimore, U.S.A.

Sunderasan, E. and Yeang, H. Y. (1994) Latex allergy studies: B-serum from the latex bottom fraction as a major source of immunogenic glove proteins. J. Nat. Rubb. Res., 8(4), 293.

Tata, S. J. and Gomez, J. B. (1980) Isolation and characterisation of microhelices from lutoids of Hevea latex. J. Rubb. Res. Inst. Malaysia, 28(2), 67.

Tupy, J. (1969) Stimulatory effects of 2,4 dichlorophenoxyacetic acid and of 1-naphthylacetic acid on sucrose level, invertase activity and sucrose utilisation in the latex. Planta, 88, 144.

Turjanmaa, K., Laurila, K., Makinen-Kiljunen, S. and Reunala, T. (1988) Rubber contact urticaria. Contact Dermatitis, 19, 362.

Turjanmaa, K., Reunala, T., Tuimala, R. and Karkkainen, T. (1984) Severe IgE-mediated allergy to surgical gloves. Allergy, 39, (Suppl. 2, Abs. 35).

Walujono, K. and Suseno, P. A. (1973) Experiments with p.a.a. electrophoresis for Hevea clones identification. Paper presented at symposium of the International Rubber Research and Development Board, Puncak, Indonesia.

Yeang, H. Y., Ghandimathi, H. and Paranjothy, K. (1977) Protein and enzyme variation in some Hevea cultivars. J. Rubb. Res. Inst. Malaysia, 25(1), 9.

Yeang, H. Y. and Paranjothy, K. (1982) Some primary determinants of seasonal yield variation in clone RRIM 623. J. Rubb. Res. Inst. Malaysia, 30(3), 131.

Yeang, H. Y. and Paranjothy, K. (1982a) Initial physiological changes in Hevea latex and latex flow characteristics associated with intensive tapping. J. Rubb. Res. Inst. Malaysia, 30(1), 31.

---

The invention claimed is:

1. An isolated monoclonal antibody developed against the allergenic protein Hev b II from latex or tissue of *Hevea brasiliensis* (Hev b), or allergenic sub-units or aggregates thereof, wherein said antibody is produced by hybridoma cell line ECAC CAMR accession number 94120727 designated USM/RB4.

* * * * *

SEQUENCE LISTING

```
<160> NUMBER OF SEQ ID NOS: 7

<210> SEQ ID NO 1
<211> LENGTH: 12
<212> TYPE: PRT
<213> ORGANISM: ARTIFICIAL SEQUENCE
<220> FEATURE:
<223> OTHER INFORMATION: SYNTHETIC CONSTRUCT

<400> SEQUENCE: 1

Val Ser Ser Tyr Leu Pro Leu Leu Pro Thr Glu Lys
1               5                   10

<210> SEQ ID NO 2
<211> LENGTH: 10
<212> TYPE: PRT
<213> ORGANISM: ARTIFICIAL SEQUENCE
<220> FEATURE:
<223> OTHER INFORMATION: SYNTHETIC CONSTRUCT

<400> SEQUENCE: 2

Gly Asp Leu Ser Thr Val Ser Arg Leu Lys
1               5                   10

<210> SEQ ID NO 3
<211> LENGTH: 19
```

```
<212> TYPE: PRT
<213> ORGANISM: ARTIFICIAL SEQUENCE
<220> FEATURE:
<223> OTHER INFORMATION: SYNTHETIC CONSTRUCT

<400> SEQUENCE: 3

Ile Val Leu Asp Val Ala Ser Ser Val Phe Asn Thr Arg Lys Gln Glu
1               5                   10                  15

Lys Gln Lys

<210> SEQ ID NO 4
<211> LENGTH: 12
<212> TYPE: PRT
<213> ORGANISM: ARTIFICIAL SEQUENCE
<220> FEATURE:
<223> OTHER INFORMATION: SYNTHETIC CONSTRUCT

<400> SEQUENCE: 4

Val Thr Pro Val Tyr Tyr Leu Gly Thr Pro Thr Val
1               5                   10

<210> SEQ ID NO 5
<211> LENGTH: 19
<212> TYPE: PRT
<213> ORGANISM: ARTIFICIAL SEQUENCE
<220> FEATURE:
<223> OTHER INFORMATION: SYNTHETIC CONSTRUCT

<400> SEQUENCE: 5

Glu Leu Asp Glu Tyr Leu Phe Ser Phe Gly Asp Gly Leu Tyr Asp Ala
1               5                   10                  15

Gly Asn Ala

<210> SEQ ID NO 6
<211> LENGTH: 11
<212> TYPE: PRT
<213> ORGANISM: ARTIFICIAL SEQUENCE
<220> FEATURE:
<223> OTHER INFORMATION: SYNTHETIC CONSTRUCT
<220> FEATURE:
<221> NAME/KEY: misc_feature
<222> LOCATION: (6)..(6)
<223> OTHER INFORMATION: Xaa can be any naturally occurring amino acid

<400> SEQUENCE: 6

Phe Asp Glu Asn Asn Xaa Gln Pro Glu Val Glu
1               5                   10

<210> SEQ ID NO 7
<211> LENGTH: 13
<212> TYPE: PRT
<213> ORGANISM: ARTIFICIAL SEQUENCE
<220> FEATURE:
<223> OTHER INFORMATION: SYNTHETIC CONSTRUCT

<400> SEQUENCE: 7

Arg Asn Ile His Asp Ala Ile Arg Ser Ala Gly Leu Gln
1               5                   10
```